(12) United States Patent
Basilico et al.

(10) Patent No.: US 6,355,781 B1
(45) Date of Patent: *Mar. 12, 2002

(54) MAMMALIAN GROWTH FACTOR

(75) Inventors: Claudio Basilico, New York, NY (US); Pasquale Delli Bovi, Portici (IT)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 08/775,567

(22) Filed: Dec. 31, 1996

Related U.S. Application Data

(63) Continuation of application No. 08/056,482, filed on May 3, 1993, now Pat. No. 5,750,659, which is a continuation of application No. 07/806,771, filed on Dec. 6, 1991, now abandoned, which is a continuation of application No. 07/177,506, filed on Apr. 4, 1998, now abandoned, which is a continuation-in-part of application No. 07/062,925, filed on Jun. 16, 1987, now abandoned.

(51) Int. Cl.$^7$ .................. C07K 14/475; C07K 14/50
(52) U.S. Cl. ........................... 530/399; 530/350
(58) Field of Search .................... 530/350, 399

(56) References Cited

U.S. PATENT DOCUMENTS 5,126,323 A * 6/1992 Rogers et al. ............... 514/12

* cited by examiner

*Primary Examiner*—Marianne P. Allen
(74) *Attorney, Agent, or Firm*—Darby & Darby

(57) ABSTRACT

A homogeneous K-FGF polypeptide having a molecular weight of about 19,000 daltons when analyzed by SDS polyacrylamide gel electrophoresis, wherein the polypeptide is substantially free of oligosaccharide moieties attached to the polypeptide, appears as a single band on SDS-PAGE, exhibits a detectable level of mitogenic activity on growth arrested cells in a $^3$H-thymidine uptake assay, and is substantially free from other mammalian proteins, is provided.

1 Claim, 15 Drawing Sheets

FIG. I

Probe G
1 2 3 4 5

— 28S
— 18S

Probe H
1 2 3 4 5

```
  1  MSGPGTAAVALLPAVLLALLAPWAGRGGAAAPTAPNGTLEAELERRWESLVALSLARLPVAAQPKEAAVQ    70
                 ─────────────────      ↑↑
                                        ***
 71  SGAGDYLLGIKRLRRLYCNVGIGFHLQALPDGRIGGAHADTRDSLLELSPVERGVVSIFGVASRFFVAMS   140
                              •
141  SKGKLYGSPFFTDECTFKEILLPNNYNAYESYKYPGMFIALSKNGKTKKGNRVSPTMKVTHFLPRL      206
                •
```

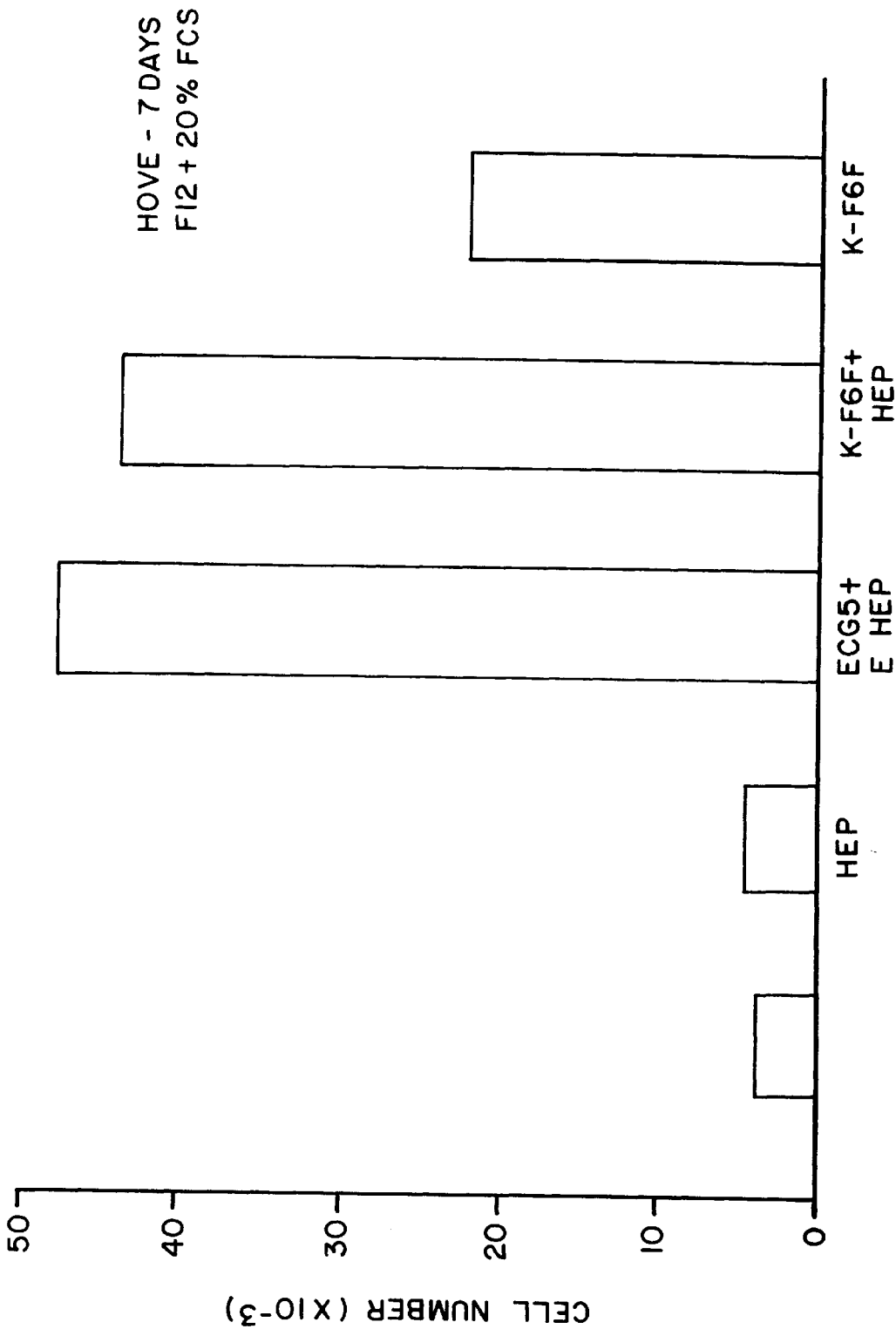

MAMMALIAN GROWTH FACTOR

This is a continuation, of application Ser. No. 08/056,482, filed May 3, 1993, now U.S. Pat. No. 5,750,659 which in turn is a continuation of Ser. No. 07/806,771, filed Dec. 6, 1991, now abandoned, which in turn is a continuation of Ser. No. 07/177,506, filed Apr. 4, 1988, now abandoned, which in turn is a continuation-in-part of Ser. No. 07/062,925, filed Jun. 16, 1987, now abandoned.

The United States Government has rights to this invention by virtue of grant No. CA-42568 from the National Institutes of Health.

BACKGROUND OF THE INVENTION

This invention is related to a novel polypeptide having mammalian growth factor activity and to methods for using it.

A variety of diffusible factors which stimulate the growth of cells in a hormone-like manner are generally called "growth factors". Growth factors are present in serum and have also been isolated from a variety of organs. They are protein molecules (or groups of such molecules) and in all known cases they interact with specific cell surface receptors to promote cellular growth and/or differentiation. Growth factors vary in their tissue specificity, i.e. some interact only with specific cell types, while others are active on a wider cell type range.

Among the best known groups of growth factors are: (1) platelet derived growth factor (PDGF), released from platelets; (2) epidermal growth factor (EGF); (3) hematopoietic growth factors (including interleukins 1, 2, and 3), required for growth and differentiation of lymphocytes, and colony stimulating factors (CSF), promoting growth and differentiation of hematopoietic stem cells; (4) angiogenic (literally "blood-vessel-forming") growth factors, such as the fibroblast growth factors (FGF) believed to promote growth and organization of endothelial cells into new blood vessels; (5) a variety of growth factors released by tumor cells and falling into two groups: alpha and beta, corresponding to their chains.

The only well-characterized angiogenic factors are basic and acidic fibroblast growth factors (FGF); believed to be most important in vivo for endothelial cell growth.

It is known that the oncogene that is characteristic of simian sarcoma virus encodes the B chain of PDGF. However, none of the remaining growth factors mentioned above are produced by oncogenes. Nor do other known oncogenes produce growth factors.

Growth factors are believed to promote wound healing. For example, EGF present in saliva is believed to accelerate wound healing in mice. Schultz G. S et al (*Science* 232:350–352, 1986) report that transforming growth factor (TGF)-alpha and vaccinia virus growth factor (VGF), both of which are substantially homologous to EGF, accelerated epidermal wound healing in pigs when topically applied to second degree burns and were significantly more active than EGF.

Of the above-mentioned growth factors, the angiogenic growth factors would be particularly useful as wound healing agents because of their ability to promote the formation and growth of new blood vessels. Preliminary evidence indicates that the two known (sequenced) angiogenic growth factors, basic and acidic FGF (so named due to the total net charge on the molecules) may be of use as wound healing agents.

OBJECTS OF THE INVENTION

It is an object of the present invention to provide a growth factor useful as a wound healing agent in mammals.

It is another object of the present invention to provide a mammalian growth factor with a tissue specificity wider than either acidic or basic FGF.

Another object is to provide novel pharmaceutical formulations and methods for promoting would healing.

These and other objects of the present invention will be apparent to those of ordinary skill in the art in light of the present description, accompanying claims and appended drawings.

SUMMARY OF THE INVENTION

The present inventors have unexpectedly discovered a single polypeptide which displays substantial homology to each of basic and acidic fibroblast growth factor, said polypeptide having growth factor activity and having an amino acid sequence consisting essentially of the amino acid sequence of the expression product of a fragment of an oncogene isolated from Kaposi's sarcoma DNA. In another aspect, the present invention is directed to a DNA molecule coding for the above polypeptide.

In yet another aspect, the present invention is directed to methods for promoting the healing of mammalian wounds or burns comprising administering to a mammal in need of such treatment a healing-promoting effective amount of the above polypeptide and to pharmaceutical formulations comprising said polypeptide and a pharmaceutically acceptable carrier or diluent.

BRIEF DESCRIPTION OF THE DRAWINGS

FIG. 13 is a bar graph showing the effect of the polypeptide of the present invention on the proliferation of human umbilical cord endothelial cells (HUVE) in culture and its potentiation by heparin.

DETAILED DESCRIPTION OF THE INVENTION

Figure 1:
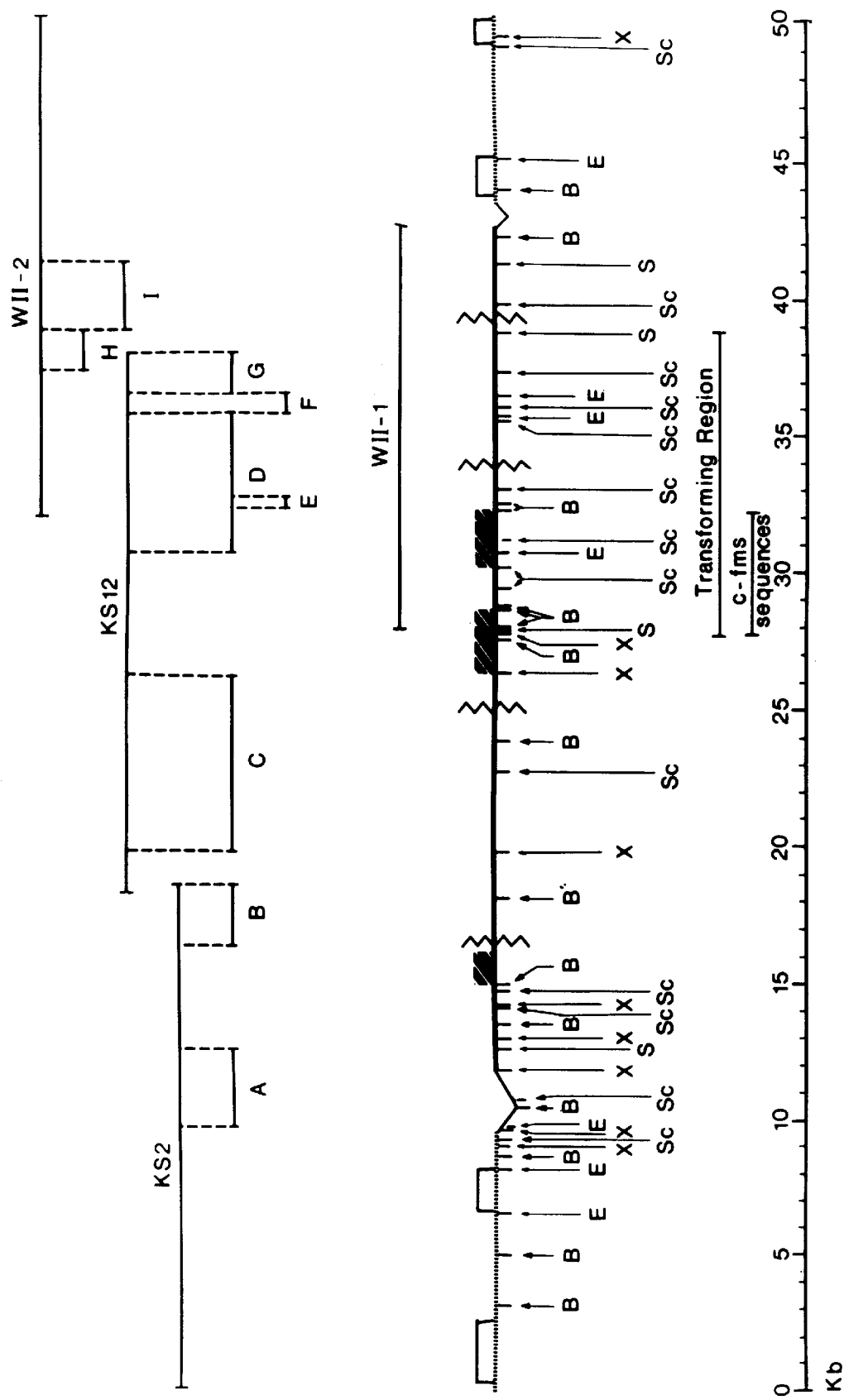
FIG. 1 is a schematic representation of the organization of the human DNA sequences (and probes made thereto) inserted into the mouse genome in the secondary Neo-2 transformant.

The present inventors have unexpectedly isolated a gene coding for a mammalian growth factor. The growth factor gene was produced when the DNA isolated from a Kaposi's Sarcoma (KS) skin lesion, obtained from a patient suffering from AIDS, was transfected into mouse cells. Kaposi's Sarcoma (KS) is a multifocal neoplastic disorder common in patients suffering from acquired immune deficiency syndrome (AIDS), and also found in other immunosuppressed individuals.

The gene of the present invention may be a novel human oncogene and one of its protein products is significantly homologous to each of the two well-known angiogenic growth factors, basic and acidic FGF and has growth factor activity. The oncogene which is "activated" in KS cells has not been heretofore identified.

The gene coding for the growth factor polypeptide of the present invention was isolated by transfecting DNA extracted from KS skin lesions of an AIDS patient into mouse NIH3T3 cells (available as ATCC CRL 1658, American Type Culture Collection, Rockville, Md.). The transfected cells' ability to produce transformed foci when cultured in vitro was then determined.

A transformed focus is a distinct clustering of visually identifiable cells arising from the uncontrolled growth of tumorigenic cells. Any cells capable of taking up and expressing foreign DNA can be employed as the recipient (the recipient cells are hereinafter referred to as primary transformants) of the DNA sequences, such as rat F2408, hamster BHK-21 or preferably mouse NIH3T3 cells.

In a preferred embodiment of the present invention, the DNA sequences encoding the growth factor can be isolated from the primary transformants and transferred to normal NIH3T3 cells in a second round of transfection (hereinafter referred to as secondary transformants) with a selectable genetic marker. The selectable genetic marker can be any gene which confers a selective growth advantage to the recipient cell. Suitable selectable markers include, but are not limited to, resistance to the antibiotic hygromycin, and preferably resistance to the antibiotic neomycin or G418 (GIBCO, Grand Island, N.Y.). Cells which are transfected by both the DNA sequence encoding the growth factor of the present invention and, for example a gene encoding resistance to G418, can then be selected for their ability to grow in the presence of concentrations of about 250 micrograms per ml of G418 present in the growth medium.

After the secondary transformants were selected for their ability to grow in the presence of neomycin, or G418 and those cells which had been transformed to the neoplastic state isolated, the human DNA sequences which had been taken up and integrated into the mouse genome were identified, molecularly cloned, using an appropriate vector (EMBL3, described in Frischauf, A. M. et al, *J. Mol. Biol.* 170: 827–842, 1983) although other vectors could have been used, and mapped by restriction endonuclease digestion, as detailed in Example 2 below. The sequences encoded in this DNA region which are transcribed into mRNA (and, presumably into protein) in these cells were identified employing the well-known Northern hybridization technique with probes obtained by restriction endonuclease digesting the cloned vector-DNA.

Two unique mRNAs, 1.2 and 3.5 Kb in length were identified, of which the 1.2 Kb species encodes the growth factor of the present invention. The sequence of this 1.2 Kb MRNA is shown in Example 5 below. The 1.2 Kb species was found to encode a polypeptide with mammalian growth factor activity. A comparison of this sequence with the known growth factor sequences revealed that it displayed substantial sequence homology with both basic and acidic FGF.

In order to determine whether a novel oncogene had been identified following the DNA mediated gene transfection, a comparison with other known viral and cellular oncogenes was performed.

The transforming DNA sequence m-RNA of the present invention did not demonstrate any sequence homology to Human Immunodeficiency Virus (the causative agent of AIDS) or cytomegalovirus DNA as well as herpes virus DNA (viruses which commonly infect AIDS patients cells, the source of the DNA sequences of the present invention). In addition, probes corresponding to a number of viral and cellular oncogenes did not hybridize (i.e. no significant sequence homology existed) with the following known oncogenes: three ras oncogenes, myc, sis, erbB, Rel, raf, myb, p53, mos and fos. However, a probe corresponding to the oncogene v-fms (isolated from feline sarcoma virus) revealed a region of homology in the cloned (i.e. 32 Kb) genomic DNA sequences. This region (indicated in FIG. 1) was homologous to a portion of the cellular fms oncogene but it is not transcribed (i.e. these sequences are not present in the novel mRNA specie described above). Therefore, the fms oncogene is not responsible for the growth factor activity of the present invention. However, the c-fms DNA sequences may contain elements which activate the expression of the growth factor sequences in the original genomic configuration in the transformants.

Once isolated, the DNA encoding the growth factor of the present invention can be cloned and the protein can be expressed in any eukaryotic or prokaryotic system known in the art. Eukaryotic expression systems, such as yeast expression vectors (described by Brake, A. et al, *Proc. Nat. Acad. Sci. USA* 81: 4642–4646, 1984), Polyoma virus based expression vectors (described in Kern, F. G. et al *Gene* 43: 237–245, 1986) or Simian virus 40 (SV40) based expression vectors in COS-1 Simian cells (as described in Gething, M. J. et al *Nature* 293: 620–625, 1981) are preferred because they are capable of secretion and of performing modifications (such as glycosylation) necessary for the production of eukaryotic proteins in their "natural" state, and do so at a high efficiency. Also, the nucleotide sequences of the growth factor of the present invention presented in Example 5 below can be used to chemically synthesize the gene using techniques known in the art.

The sequence of the expression product of the present invention has been derived from the DNA sequence. The polypeptide of the present invention can be prepared by techniques known in the art. In addition, by routine experimentation (involving modification of the DNA sequences) the minimum polypeptide sequence having growth factor activity can be identified. In addition, other modifications to the amino acid sequence of the present polypeptide may be made provided that they do not affect the growth factor activity of said polypeptide. The polypeptide of the present invention has a sequence that corresponds to the expression product of a fragment of the oncogene from which the present polypeptide was identified. This is an advantage because the entire expression product of the oncogene need not be produced. Without wishing to be bound by theory, it is believed that the polypeptide of the present invention is similar to, if not identical with, its cellular protooncogene.

The present inventors have also found that the growth factor of the present invention stimulated proliferation and plasminogen activator production in endothelial cells in culture. It has also been found that heparin is required for the above-mentioned effects to be manifested in endothelial cells, but not in cells of fibroblast origin. In human cord vein endothelia, heparin potentiates the effect, but is not essential. It is believed that heparin may protect the mammalian growth factor from degradation and/or assist in the formation of a temperature table complex. Therefore, pharmaceutical formulations comprising the mammalian growth factor of the present invention may also contain an effective amount of heparin or fragments thereof as a stabilizing agent. The amount of heparin to be added can be obtained by routine experimentation well known in the art.

Studies described below in Example 9 show that the mammalian growth factor of the present invention may be provided as a secreted glycoprotein and is processed in mammalian cells so that approximately 30 amino acids (representing a signal sequence) are removed in order to form the mature protein. Therefore, the mammalian growth factor can be obtained from the conditioned medium of mammalian cells transfected with the DNA sequences encoding this glycoprotein, such as COS-1 cells described below.

The mammalian growth factor of the present invention can be employed as a wound-healing agent for various wounds, such as decubitus ulcers or burns. When employed as a wound or burn healing agent, the growth factor of the present invention may be administered to a mammal in need of such treatment orally, parenterally, or preferably, topically, directly to the affected area in amounts broadly ranging between about 10 nanograms and about 10 micrograms per dose. The number of treatments and the duration can vary from individual to individual depending upon the severity of the wound or burn. A typical treatment would comprise 2 or 3 applications per day, topically administered directly to the wound or burn.

The growth factor of the present invention can be prepared in pharmaceutical formulations to be used as a wound or burn healing agent. Pharmaceutical formulations comprising the mammalian growth factor of the present invention (or physiologically acceptable salts thereof) as at least one of the active ingredients, would in addition contain pharmaceutically-acceptable carriers, diluents, fillers, salts and other materials well-known in the art depending upon the dosage form utilized. For example, parenteral dosage forms would comprise a physiologic, sterile saline solution. Such formulations may also contain heparin or fragments thereof as stabilizing agents. In a particularly preferred embodiment, the mammalian growth factor of the present invention may be mixed with antibiotic creams (such as Silvadene, Marion Laboratories, Kansas City, Mich., Achromycin, Lederle Laboratories, Pearl River, N.Y., or Terramycin, Pfipharmecs, New York, N.Y.) well-known in the art.

Although the growth factor of the present invention is particularly useful as a wound or burn healing agent, it additionally can be employed as a growth promoting agent for cells in tissue culture and/or as a partial serum substitute. The growth-promoting properties are illustrated in Example-6 below.

The invention is described further below and specific examples which are intended to illustrate the present invention without limiting its scope.

EXAMPLE 1: TRANSFECTION OF NIH3T3 CELLS

High molecular weight DNA was extracted from one KS skin lesion, as described in Delli Bovi, P. et al, *Cancer Res.* 46: 6333–6338, 1986, (incorporated by reference) and transfected into NIH3T3 cells using the well-known calcium phosphate precipitation technique (Graham, F. L. et al *Virology* 52: 456–467, 1973). A distinct focus of highly retractile cells was produced over the background of non-transfected NIH3T3 cells indicating the presence of transformed cells. To insure the homogeneity of the cell population, cells from the primary focus were recloned in agar suspension medium (Stoker, M. et al *Nature* 203: 1355–1357, 1964 incorporated by reference) since only transformed cells are capable of such growth.

Southern blot hybridization, performed with the Blur-8 plasmid (Jelinek, W. R. et al *Proc. Nat. Acad. Sci. USA* 77: 1398–1402, 1980 incorporated by reference), containing DNA sequences representative of the AluI family of repetitive DNA (a repetitive DNA sequence present in and indicative of DNA isolated from human cells), revealed that all cells which were transformed were capable of growth in agar had acquired human DNA sequences.

Cells from one agar colony isolated as above, were injected into athymic mice (106 cells per mouse) and two out of three mice developed tumors. DNA from one of the tumors (A15T) was used to transfect NIH3T3 cells together with a selectable marker, plasmid pIW3 (Pellegrini, S. et al *Cell.* 36: 943–949, 1984 incorporated by reference) which contains sequences conferring resistance to the aminoglycoside antibiotic G418 (a neomycin derivative). Mammalian cells, such as NIH3T3 cells, are sensitive to and are killed by these aminoglycoside antibiotics. However, plasmid pIW3 encodes a gene which allows cells to grow in the presence of neomycin or G418. Selection for cells resistant to G418 revealed the presence of two colonies with transformed morphology, such as a disorganized piling of cell, and a loss of contact inhibition of growth, while selection for focus formation also resulted in the isolation of two morphologically transformed foci.

DNA from one of the colonies resistant to G418 was used for a third cycle of NIH3T3 transfection and again produced a small but significant number of AluI positive transformed foci. This demonstrated that the human DNA sequences identified and used to transfect NIH3T3 cells were capable of reproducibly transforming these cells, since the transformed phenotype correlated with the presence of the human AluI repetitive DNA in every stage of the assay.

EXAMPLE 2: MOLECULAR CLONING

A genomic library of DNA extracted from one of the neomycin-resistant secondary transformants (Neo-2) was constructed after endonuclease MboI partial digestion and cloned into the EMBL3 lambda phage vector (Frischauf, A. M. et al *J. Mol. Biol.* 170: 827–842, 1983 incorporated by reference). The library was screened for the presence of recombinant phages containing human AluI repetitive DNA by plating the recombinant phages on a lawn of phage-susceptible bacteria, and allowing them to form plaques of bacterial lysis. Phage DNA was collected from the individual lysates and transferred to nitrocellulose filters (Schleicher and Schul, Keene, NH) and hybridized with a nick-translated, $^{32}$P-labeled purified 300 basepair BamHI restriction fragment from plasmid Blur-8 (as described in Maniatis et al, *Molecular Cloning: A Laboratory Manual.* Cold Spring Harbor Lab, NY, 1982). One recombinant phage (KS-2) was isolated by this procedure. Hybridization with the Blur-8 AluI plasmid and total mouse DNA revealed that it contained one AluI sequence and two stretches of repetitive mouse DNA sequences and, thus represented one of the junctions between mouse and human DNA in the secondary Neo-2 transformant.

Several restriction enzyme fragments indicated in FIG. 1 were used to perform two further rounds of screening of the same library by hybridization to the above-mentioned DNA fragments. Several recombinant phages were thus isolated which appeared to span the entire insertion of human DNA into the Neo-2 transformant. The restriction map of the human genomic DNA sequences present in the transfected cells as reconstructed from four overlapping recombinant phages among those isolated is shown in FIG. 1.

In FIG. 1, A, B, C, D, E, F, G, H, and I in the upper part of the figure represent DNA fragments derived from the phages shown and used in the characterization of these sequences by Southern and Northern blotting analysis. The interrupted lines indicate mouse DNA. The continuous dark lines indicate human DNA. The "V" indicates the regions of joining between mouse and human DNA. Open boxes indicate regions containing mouse repetitive DNA. The hatched boxes indicate the regions containing the human AluI repetitive DNA sequences. Squiggles indicate the approximate sites of DNA rearrangements. Restriction sites are indicated as follows: E, EcoR1; B, BamHI; X, XbaI; S, SaiII, Sc, SacI.

The restriction map presented in FIG. 1 encompasses approximately 32 Kb (from the X at approximately 12 Kb to just before the V at the 43 Kb marker in FIG. 1) of human DNA and contains 3 AluI sequences. Several DNA fragments derived from these sequences in FIG. 1 were used to determine the presence and arrangement of the transfected human DNA in primary and secondary transformants, as well as in normal human DNA. Southern blot hybridization using these probes revealed that all these sequences studied were present in the secondary and tertiary transformants, in the two primary tumors, and also in the DNA isolated from the primary focus (primary transformant). Restriction enzyme analysis and blot hybridization of the cloned human sequences revealed that they contained four rearrangements with respect to normal human DNA, i.e. they were derived from the junction of five DNA fragments which are normally not contiguous in the human genome.

EXAMPLE 3: TRANSCRIPTION OF HUMAN SEQUENCES PRESENT IN NIH3T3 TRANSFORMANTS

In order to detect whether the specific human sequences present in the secondary NIH3T3 transformants were transcribed into mRNAs (and presumably translated into protein) in the transfected NIH3T3 cells, several of the DNA fragments indicated in FIG. 1 (A through H) were used as probes in Northern blot hybridization. Total RNA from the secondary transformants was extracted and purified by the guanidinium-cesium chloride method as described in Kern, F. G. et al *Mol. Cell. Biol.* 5: 797–807, 1985 incorporated by reference. Poly (A)+RNA was selected (using Hybond m-AP paper, Amersham, Arlington Heights, Ill.), and RNAs were fractionated in the presence of formaldehyde by agarose gel electrophoresis and transferred to nitrocellulose filters as described by Maniatis et al. (supra). Nucleic acid hybridization, washing and autoradiography were performed as described in Kern et al (supra). The results are shown in FIGS. 3A and 3B.

Figure 3A:
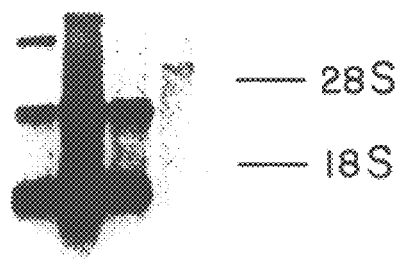
FIGS. 3A and 3B are autoradiographs of Northern blots showing the novel mRNA species encoding the polypeptide of the present invention.
Figure 3B:
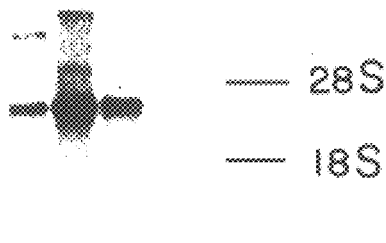

FIGS. 3A and 3B show the results of the Northern blots using probes G and H to detect novel mRNA species in transformants by hybridization to 1.5 micrograms of poly (A)+RNA prepared from NIH3T3(lane 1); secondary transformant (designated F1A1) (lane 2); secondary transformant (Neo-2) (lane 3); A15T tumor cells (lane 4); human umbilical vein endothelial cells transformed by SV40 (designated HUVE-SV, lane 5).

Figure 2:
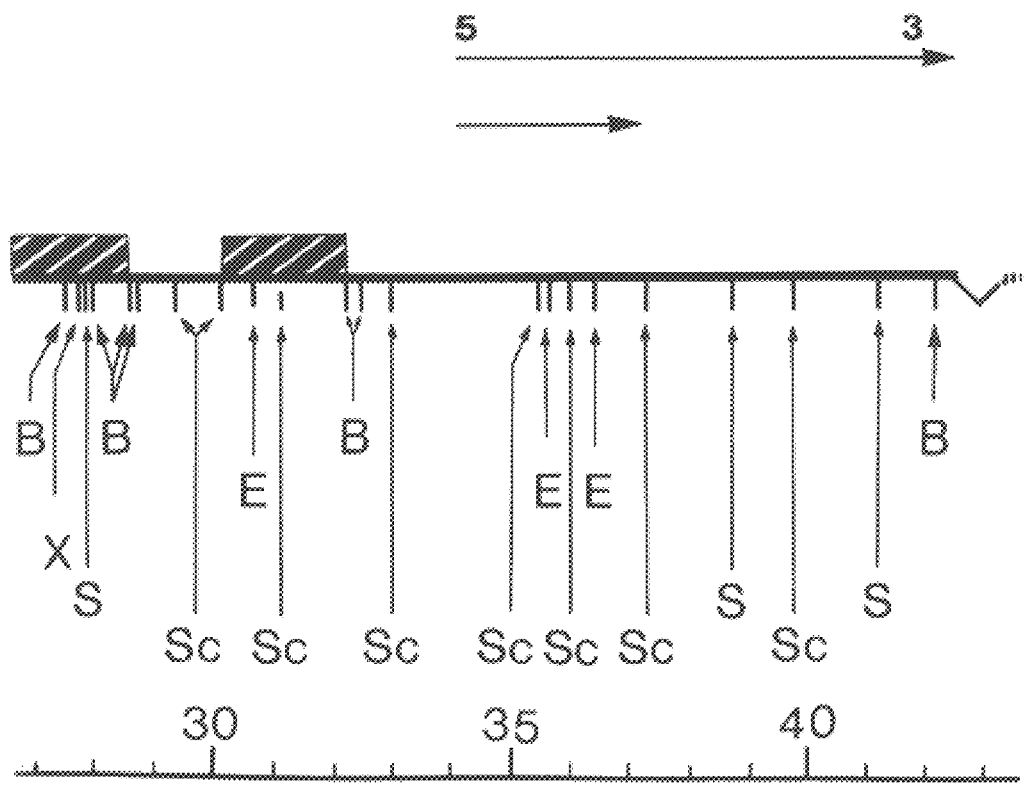
FIG. 2 is a schematic representation of the specific region of human DNA sequences shown in FIG. 1 encoding the polypeptide of the present invention.

Probes A, B, C, D, and E (identified in FIG. 1) did not hybridize with any distinct mRNA species among the poly (A)+RNAs extracted from primary or secondary transformants. Probes F and G hybridized with two novel mRNA species of about 1.2 and 3.5 Kb (FIG. 3A) in primary and secondary transformants and also with some larger RNA species of variable length in some of the cell lines tested (e.g., lanes 2 and 3). These probes did not detect any distinct RNA species in normal, non-transfected NIH3T3 cells (lane 1) and only a faint band of approximately 4 Kb in length in the RNA extracted from human endothelial cells (lane 5,). Probe H. recognized only the longer mRNA, but not the 1.2 Kb species (FIG. 3B). Thus, it appeared that the transcribed sequences were restricted to about 10 Kb of human DNA, and they were expressed in these two novel species of mRNA which contain common and unique sequences. An enlargement of the map of FIG. 1 showing the region encoding these sequences is shown in FIG. 2 (indicated by the arrow 5'-3').

EXAMPLE 4: BIOLOGICAL ACTIVITY

Figure 4A:
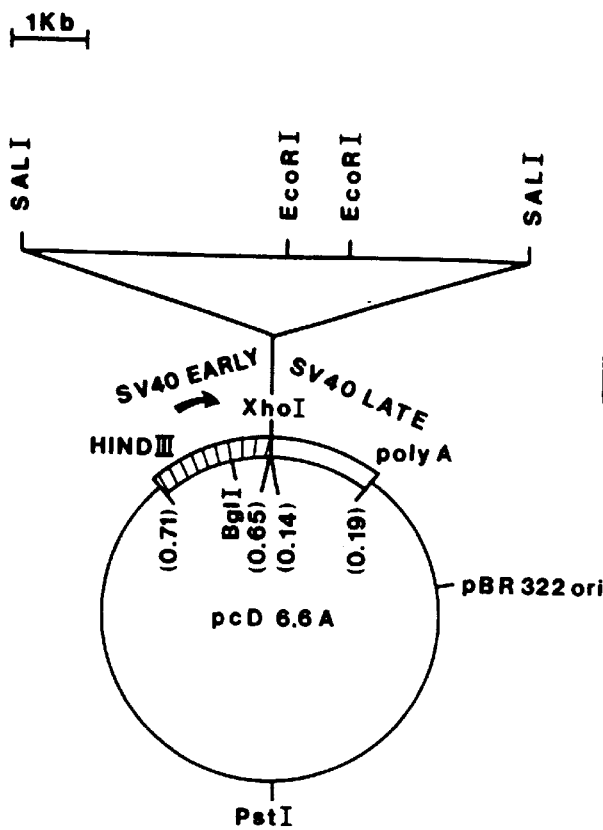
FIGS. 4A–C are schematic representations of the plasmids used in cloning the genomic DNA fragments and the cDNA encoding the polypeptide of the present invention.
Figure 4B:
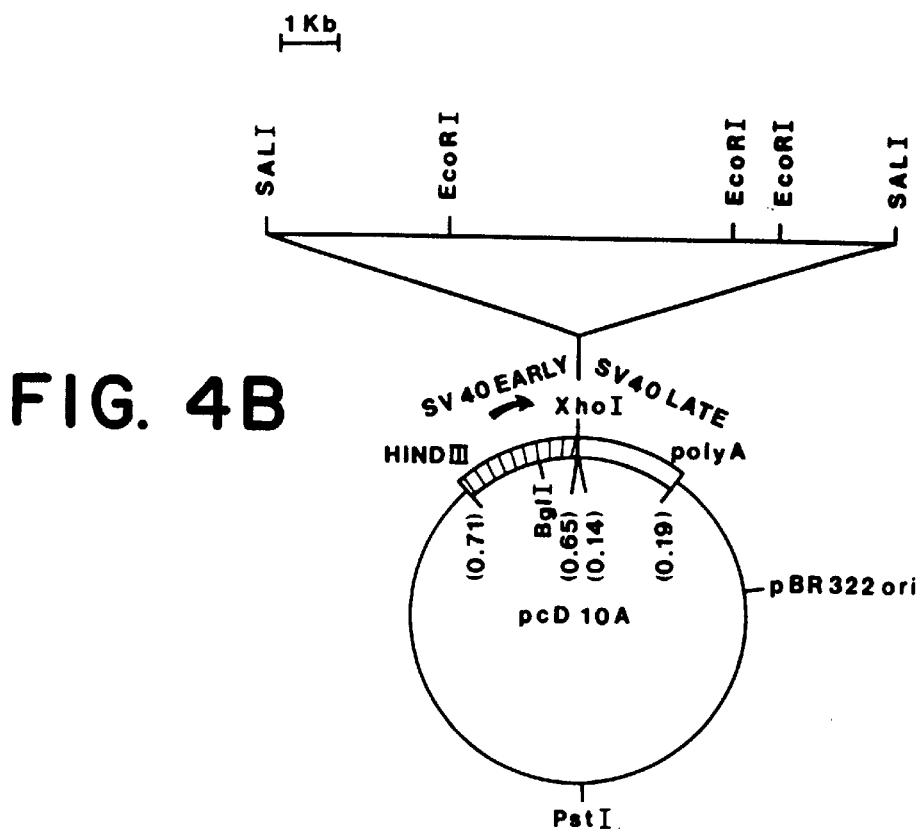

To map more precisely the transforming DNA sequences, a 11 Kb fragment going from the left polylinker SalI (at about 28 Kb in FIG. 2) site of phage WII-1 rightward to the next SalI site (FIG. 2) was subcloned into the XhoI site of the pCD SV40 expression vector (Okayama, H. et al, *Mol. Cell. Biol* 3: 280–289, 1983, incorporated by reference), in both orientations with respect to the SV40 promoter, and the resulting plasmids (pCD6.6A and pCD10A, shown in FIGS. 4A and 4B) were tested for their biological activity. Both plasmids produced transformed foci on mouse NIH3T3 cells and rat F2408 cells with an efficiency comparable to that of a control plasmid (pTB-1) containing an activated ras oncogene (as described in Goldfarb, H. et al, *Nature* 296: 404–409, 1982 incorporated by reference).

Cells (approximately 1×10$^6$ per dish) were transfected using the calcium phosphate precipitation technique as described above with the plasmid DNA together with 20 micrograms of mouse carrier DNA. Each culture was then subdivided into five plates. Foci were counted at 2–3 weeks after transfection. The results are presented below in Table I.

TABLE I

Transformation of Mouse and Rat Fibroblasts with Recombinant Plasmid DNAs

| Plasmids | Foci/microgram DNA | |
|---|---|---|
| | NIH3T3 | Rat F2408 |
| EXPT. I | | |
| pCD (WII-1) 10 A* | 900 | 192 |
| pCD (WII-1) 10 B* | 800 | — |
| pGEM (WII-1) 10 | 120 | — |
| pTB-1 (ras) | 800 | 520 |
| EXPT. II | | |
| pCD (WII-2) 6.6 A* | 2500 | 150 |
| pCD (WII-2) 6.6 B* | 1400 | 80 |
| pGEM (WII-2) 6.6 | 40 | — |
| pTB-1 | 2500 | 400 |
| EXPT. III | | |
| pTB-1 | 500 | — |
| p9BKS3A** | 2000 | — |
| p9BKS3B** | <1 | — |
| pCD (WII-1) 10 A | 1400 | — |

*A and B indicate the position of the SV40 promoter/enhancer element with respect to the polarity of transcription (going from left to right in FIG. 1) of the inserted SalI genomic fragments contained in the pCD expression vector. The "A" constructs have the SV40 promoter/enhancer in 5' position and the "B" constructs in 3' position.
**The p9BKS3 plasmids contain the cDNA encoding the growth factor of the present invention in the 5'-3' polarity (A) or 3'-5' polarity (B).

As can be seen from Table I above, the same DNA fragment was capable of producing transformed foci when inserted into the pCD and pGEM3 bacterial vector (the latter available from Promega Biotech, Madison, Wis.), but in the case of the pGEM3 vector, with about 8-fold lower efficiency.

A 6.6 Kb DNA fragment going from the left SalI site of phage WII-2 to the same SalI site used for the above-mentioned constructs FIG. 1) was also cloned using both pCD and pGEM vectors. The pCD-6.6 constructs transformed both mouse and rat cells with high efficiency similar to that of pTB-1 and that of the pCD10 plasmids, whereas the pGEM constructs were transformed with an efficiency about 40 fold lower (Experiment II, Table I). Therefore the 6.6 Kb fragment appeared to contain all of the sequences encoding a transforming gene and also a transcriptional promoter since it functioned in a plasmid vector devoid of any mammalian transcriptional regulatory elements. The higher efficiency of transformation of the pCD plasmids is probably due to the presence of the SV40 "enhancer" sequences.

EXAMPLE 5: C-DNA CLONING

To precisely identify the DNA sequences responsible for the growth factor activity of the cloned DNA products, a complementary DNA (cDNA) library was constructed from the poly(A)+RNA isolated from one of the transformants (A15T). This library was constructed in a bacteriophage lambda gt10 vector (Huynh, T. V. et al in *DNA Cloninq: A Practical Approach* D. Glover, ed. Vol 1: 49–78, Oxford Press, 1985 incorporated by reference), and the recombinant phages plaques (from Example 2) screened with the probes G and H (in FIG. 1). The library was constructed using a cDNA synthesis system (Amersham Corporation, Arlington Heights, IL) and the poly(A)+RNA obtained from the AI5T cell line isolated by the guanidiumisothiocyanate procedure as described in Example 3 above. Following methylation with EcoRI methylase and the addition of EcoRI linkers, the linkers were digested and the cDNA size-fractionated by column chromatography (A50m column, BioRad, Richmond, Calif.). The cDNA was then ligated to EcoRI digested, dephosphorylated lambda-gt10 arms (Promega Biotech, Madison, Wis.). The ligated cDNA was then packaged (using Gigapack extracts, Stratagene Cloning Systems, San Diego, Calif.) and plated, using C600 Hf1 (*E.coli*) as a host strain. A cDNA corresponding to the 1.2 Kb mRNA was isolated by plaque hybridization to probe G.

Subcloning of the cDNA insert cD3, a clone which contained the cDNA corresponding to the 1.2 Kb mRNA above, into mammalian expression vector 91023B (Kauffman, R. J. *Proc. Nat. Acad. Sci. USA* 82: 689–693, 1985 incorporated by reference) produced plasmid p9BKS3A and its biological activity was confirmed, i.e. it was capable of transforming NIH3T3 cells with a high efficiency upon transfection (Table I, Expt III). This cDNA was also subcloned into pGEM-3 sequencing vector (Promega Biotec, Madison, Wis.) and sequenced by the dideoxy method of Sanger, F. (*Proc. Nat. Acad. Sci. USA* 74: 5463–5467, 1977 incorporated by reference) and in part by the method of Maxam, A. U. and Gilbert, W. (*Methods Enzymol* 65: 499–560, 1980, incorporated by reference). The nucleotide sequence is presented below.

```
            10          20          30          40
             *           *           *           *
GG CGC GCA CTG CTC CTC AGA GTC CCA GCT CCA GCC GCG CGC TTT CCG 50          60          70          80          90
 *           *           *           *           *
CCC GGC TCG CCG CTC CAT GCA GCC GGG GTA GAG CCC GGC GCC CGG GGG 100         110         120         130         140
     *           *           *           *           *
CCC CGT CGC TTG CCT CCC GCA CCT CCT CGG TTG CGC ACT CCC GCC CGA 150         160         170         180         190
         *           *           *           *           *
GGT CGG CCG TGC GCT CCC GCG GGA CGC CAC AGG CGC AGC TCT GCC CCC 200         210         220         230
             *           *           *           *
CAG CTT CCC GGG CGC ACT GAC CGC CTG ACC GAC GCA CGC CCT CGG GCC 240         250         260         270         280
```

-continued

```
         *              *              *              *              *
GGG ATG TCG GGG CCC GGG ACG GCC GCG GTA GCG CTG CTC CCG GCG GTC
—et Ser Gly Pro Gly Thr Ala Ala Val Ala Leu Leu Pro Ala Val 290            300            310            320            330
     *              *              *              *              *
CTG CTG GCC TTG CTG GCG CCC TGG GCG GGC CGA GGG GGC GCC GCC GCA
Leu Leu Ala Leu Leu Ala Pro Trp Ala Gly Arg Gly Gly Ala Ala Ala 340            350            360            370            380
         *              *              *              *              *
CCC ACT GCA CCC AAC GGC ACG CTG GAG GCC GAG CTG GAG CGC CGC TGG
Pro Thr Ala Pro Asn Gly Thr Leu Glu Ala Glu Leu Glu Arg Arg Trp 390            400            410            420            430
             *              *              *              *              *
GAG AGC CTG GTG GCG CTC TCG TTG GCG CGC CTG CCG GTG GCA GCG CAG
Glu Ser Leu Val Ala Leu Ser Leu Ala Arg Leu Pro Val Ala Ala Gln 450            460            470
                            *              *              *
CCC AAG GAG GCG GCC GTC CAG AGC GGC GCC GGC GAC TAC CTG CTG GGC
Pro Lys Glu Ala Ala Val Gln Ser Gly Ala Gly Asp Tyr Leu Leu Gly 480            490            500            510            520
 *              *              *              *              *
ATC AAG CGG CTG CGG CGG CTC TAC TGC AAC GTG GGC ATC GGC TTC CAC
Ile Lys Arg Leu Arg Arg Leu Tyr Cys Asn Val Gly Ile Gly Phe His 530            540            550            560            570
     *              *              *              *              *
CTC CAG GCG CTC CCC GAC GGC CGC ATC GGC GGC GCG CAC GCG GAC ACC
Leu Gln Ala Leu Pro Asp Gly Arg Ile Gly Gly Ala His Ala Asp Thr 580            590            600            610            620
         *              *              *              *              *
CGC GAC AGC CTG CTG GAG CTC TCG CCC GTG GAG CGG GGC GTG GTG AGC
Arg Asp Ser Leu Leu Glu Leu Ser Pro Val Glu Arg Gly Val Val Ser 630            640            650            660            670
             *              *              *              *              *
ATC TTC GGC GTG GCC AGC CGG TTC TTC GTG GCC ATG AGC AGC AAG GGC
Ile Phe Gly Val Ala Ser Arg Phe Phe Val Ala Met Ser Ser Lys Gly 680            690            700            710
                 *              *              *              *
AAG CTC TAT GGC TCG CCC TTC TTC ACC GAT GAG TGC ACG TTC AAG GAG
Lys Leu Tyr Gly Ser Pro Phe Phe Thr Asp Glu Cys Thr Phe Lys Glu 720            730            740            750            760
 *              *              *              *              *
ATT CTC CTT CCC AAC AAC TAC AAC GCC TAC GAG TCC TAC AAG TAC CCC
Ile Leu Leu Pro Asn Asn Tyr Asn Ala Tyr Glu Ser Tyr Lys Tyr Pro 770            780            790            800            810
 *              *              *              *              *
GGC ATG TTC ATC GCC CTG AGC AAG AAT GGG AAG ACC AAG AAG GGG AAC
Gly Met Phe Ile Ala Leu Ser Lys Asn Gly Lys Thr Lys Lys Gly Asn 830            840            850            860
                 *              *              *              *
CGA GTG TCG CCC ACC ATG AAG GTC ACC CAC TTC CTC CCC AGG CTG TGA
Arg Val Ser Pro Thr Met Lys Val Thr His Phe Leu Pro Arg Leu ---

870            880            890            900            910
         *              *              *              *              *
CCC TCC AGA GGA CCC TTG CCT CAG CCT CGG GAA GCC CCT GGG AGG GCA 920            930            940            950
             *              *              *              *
GTG CGA GGG TCA CCT TGG TGC ACT TTC TTC GGA TGA AGA GTT TAA TGC 960            970            980            990            1000
 *              *              *              *              *
AAG AGT AGG TGT AAG ATA TTT AAA TTA ATT ATT TAA ATG TGT ATA TAT 1010           1020           1030           1040           1050
 *              *              *              *              *
TGC CAC CAA ATT ATT TAT AGT TCT GCG GGT GTG TTT TTT AAT TTT CTG
```

-continued

```
      1060            1070           1080          1090          1100
        *              *              *             *             *
GGG GGA AAA AAA GAC AAA ACA AAA AAC CAA CTC TGA CTT TTC TGG TGC 1110            1120           1130          1140
        *              *              *             *
AAC AGT GGA GAA TCT TAC CAT TGG ATT TCT TTA ACT TGT
```

The above nucleotide sequence is unusual in many respects. It is extremely G-C rich (75–85%) in approximately the first 650 nucleotides (5'-3') while its 3' part is rich in sequences of the ATTT(A) type characteristic of unstable mRNAs. There was only one open reading frame (encoding a protein) with an in-frame ATG (the initiation codon for protein translation) which would encode a protein comprising 206 amino acids. Analysis of the predicted protein sequences revealed a significant (substantial) homology (approximately 45%) to mature bovine basic as well as human basic FGF as described by Abraham, J. A. et al (*Science* 233: 545–548, 1986; *EMBO J.* 5: 2528, 1986). A less stringent (but still substantial) homology (approximately 35%) was noted with respect to bovine acidic FGF whose sequences was described in Gimenez-Gallego, G. et al, *Science* 230: 1385, 1985. If one takes into account not only amino acid identity, but also conserved substitutions, the deduced homology becomes higher (approximately 65% and 60% for basic and acidic FGF, respectively). The first portion of the growth factor of the present invention (approximately 70 amino acids) did not demonstrate any homology to the two FGF primary sequences and strictly speaking may not be necessary for growth factor activity. This portion contained a possible signal peptide important for secretion of secretory proteins. A comparison of the protein sequence of the growth factor of the present invention and those of bovine basic and acidic FGF is shown below in Table II.

TABLE II

BOVINE BASIC FIBROBLAST GROWTH FACTOR

1' MSGPGTAAVALLPAVLLALLAPWAGRG-
   GAAAPTAPNGTLEAELERRWESLVALSLARLPV
61' AAQPKEAAVQSGAGDYLLG-IKRLRRLYCNVGIGFHLQALPDGRIGGAHADTRDSL-
    LEL
1" PALPEDGGSGAFPPGHFKDPKRLYCKNG-GFFLRIHPDGRVDGVREKSDPHIKLQL
119' SPVERGVVSIFGVASRFFVAMSSKGK-
     LYGSPFFTDECTFKEILLPNNYNAYESYKYPGMF
56" QAEERGVVSIKGVCANRYLAMKEDGRL-
    LASKCVTDECFFFERLESNNYNTYRSRKYSSWY
179' IALSKNGKTKKGNRVSPTMKVTHFLPRL
116" VALKRTGQYKLGPKTGPGQKAILFLPMSAKS

BOVINE ACIDIC FIBROBLAST GROWTH FACTOR

1' MSGPGTAAVALLPAVLLALLAPWAGRG-
   GAAAPTAPNGTLEAELERRWESLVALSLARLPV
61' AAQPKEAAVQSGAGDYLLGIKRLRRLYCNVGIGFHLQALPDGRIGGAHADTRDSL-
    LELS
1" FNLPLGNYKKPKLLYCSNG-GYFLRILPDGTVDGTKDRSDQHIQLQLC
120' PVERGVVSIFGVASRFFVAMSSKGKLYGSPFFTDECTFKEILLPNNYNAYESYKYPGM--
48" AESIGEVYIKSTETGQFLAMDTDGLLYG-
    SQTPNEECLFLERLEENHYNTYISKKHAEKHW
178' FIALSKNGKTKKGNRVSPTMKVTHFLPRL
108" FVGLKKNGRSKLGPRTHFGQKAILFLPLPVSSD

A = Ala; R = Arg; N = Asn; D = Asp; C = Cys; Q = Gln; E = Glu
G = Gly; H = His; I = Ile; L = Leu; K = Lys; M = Met; F = Phe
P = Pro; S = Ser; T = Thr; W = Trp; Y = Tyr; V = Val.

In Table II, two dots between a particular set of amino acid residues indicate exact identity between the growth factor of the present invention and either one of the basic or acidic FGF, and one dot indicates a conservative substitution, e.g. substitution of the same type of amino acid. In addition, the amino acid sequence of the growth factor of the present invention is presented as the sequences numbered 1'–206', while the FGF sequences are presented as the sequences numbered 1"–146" and 1"–141" for basic and acidic FGF, respectively.

EXAMPLE 6: BIOLOGICAL ACTIVITY OF MEDIUM OBTAINED BY THE GROWTH OF TRANSFECTED CELLS

In order to demonstrate that cells transfected with the 1.2 Kb cDNA sequences indeed produce the growth factor of the present invention, the media obtained from culturing the NIH3T3 transformants were tested for ability to stimulate cell proliferation and/or to induce in these cells properties typical of transformed cells in vitro (e.g. changes in morphology, ability to grow in suspension in medium containing 0.34% agar). Medium conditioned by incubating monolayer cultures of two transformed cell lines (A15T and 91B3-1) for twenty hours in Dulbecco's modified Eagle's medium (DMEM, GIBCO, Grand Island, N.Y.) plus 0.4% serum was applied to cultures of normal NIH3T3 cells which had been plated in 0.4% calf serum. The medium caused striking morphologic changes in the cells, indicative of transformed cells. When the cell number was measured after six days in culture, the control cultures (kept in 0.4% serum without any other additions) showed practically no growth during this time, while cells incubated in conditioned medium doubled in number every 48 hours.

Figure 4C:
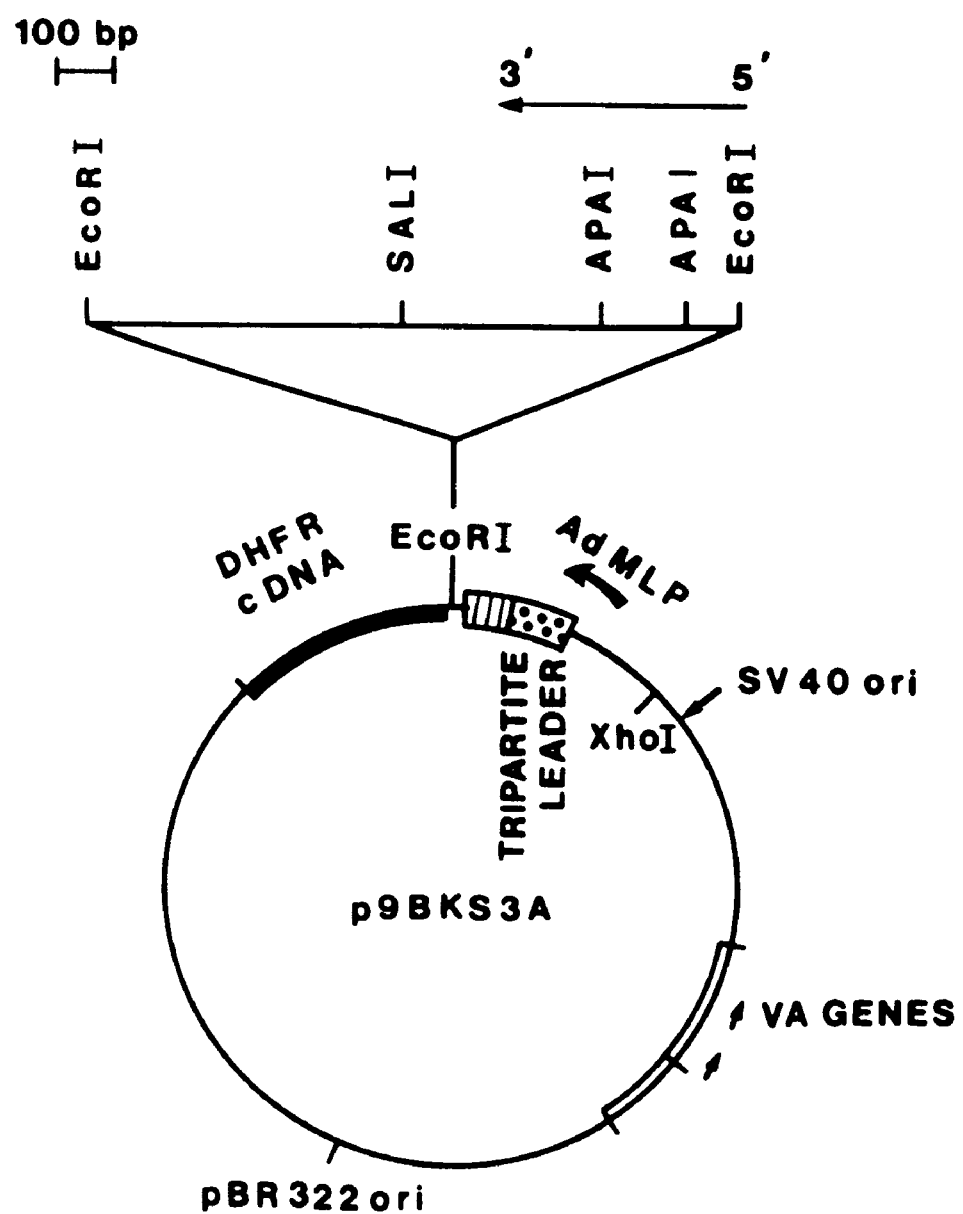

The ability of the cells transfected with the growth factor of the present invention to secrete the protein was tested in the following manner: NIH3T3 cells transformed with p9BKS3A (shown in FIG. 4C) or the A15T primary transformant cell line were plated on the bottom of a 50 mm petri dish, allowed to grow until semi-confluent, and then covered with 7 mls of agar-containing medium. After this agar layer was hardened, a new thin layer (1.5 ml) of agar medium containing 20,000 normal hamster BHK-21 cells (available as ATCC CCL 8, American Type Culture Collection, Rockville, MD) was added. In this way the cells attached to the bottom of the dish metabolize and still grow to some extent, but they cannot enter in physical contact with the BHK-21 cells of the upper layer. Controls were BHK-21 cells without a "feeder" layer or NIH3T3 cells transformed by an "activated" ras oncogene (PTB1), an oncogene known to transform these cells. Plates were incubated at 37° C. for about twelve days. The results are shown in FIGS. 5A–D.

Figure 5A:
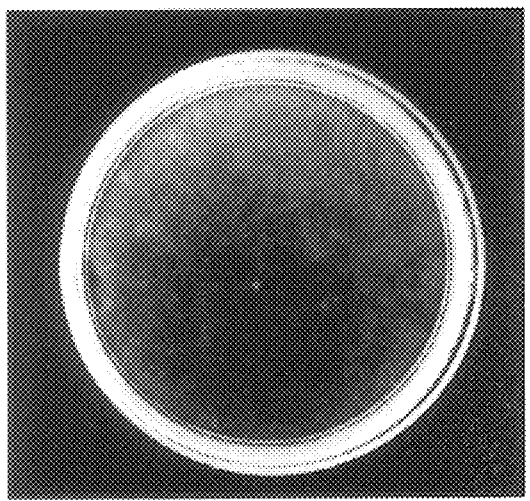
FIGS. 5A–D are series of photographs demonstrating the promotion of growth in agar of hamster BHK-21 cells superimposed on a layer of cells transformed in accordance with present the invention.
Figure 5B:
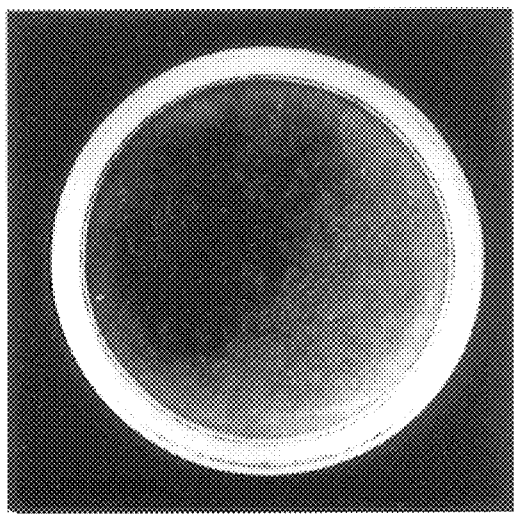
Figure 5C:
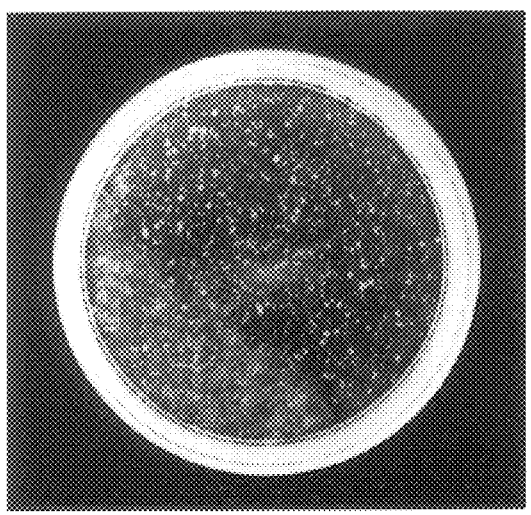
Figure 5D:
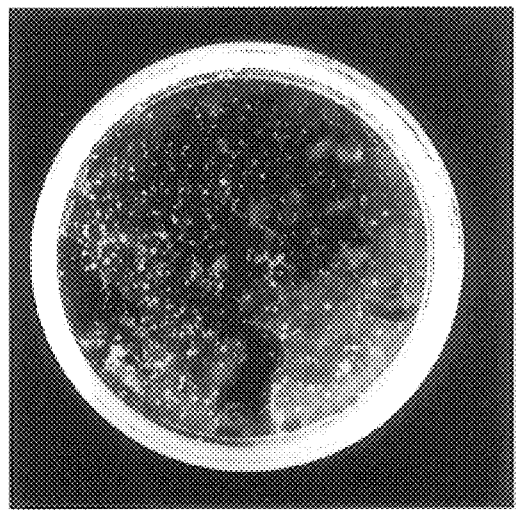

No agar growing colonies of BHK-21 cells were observed in negative controls (FIG. 5A) while the ras-transformed cells induced the growth of only about 100 microcolonies (FIG. 5B). However, both the A15T cell line and cells transformed by p9BKS3A plasmids secreted a factor which induced the formation of very large colonies in 50 to 90% of the BHK-21 cells present in the agar overlay (FIGS. 5C and 5D).

EXAMPLE 7: EXPRESSION OF THE GROWTH FACTOR OF THE PRESENT INVENTION IN BACTERIAL CELLS

To prove conclusively that the growth factor of the present invention was encoded in the CDNA sequences (approximately 1.2 Kb in length discussed above), the sequences were expressed in *E. coli* under the control of an inducible bacterial expression vector.

The vector used was pEx34C (a derivative of pEx31, described in Strebel, K. et al. *J. Virol.* 57: 983–991, 1986 incorporated by reference) which contains the DNA sequences encoding the N-terminal 99 amino acids of the polymerase of RNA bacteriophage MS2 under the control of an inducible bacteriophage lambda PL promoter. The vector was cut with restriction endonuclease BamHI, the ends blunted using the Klenow fragment of DNA polymerase, and the blunt-end was ligated to SmaI-cut cDNA contained in the pGEM-3 vector. SmaI cuts the cDNA at nucleotide 254 (see sequence) and then downstream in the polylinker region of the pGEM-3 plasmid. Using the pEx34C vector, a fusion gene was constructed which encoded a fusion protein of approximately 30,000 daltons, comprising the first 99 amino acids of the bacteriophage MS2 polymerase followed by all amino acids encoded by the cDNA inserted except the first four. Induction of expression in the appropriate bacterial host (by raising the temperature to 42° C., as described in Strebel, et al, supra) resulted in the synthesis of large amounts of a protein of the expected molecular weight, which was absent under non-induced conditions as evidenced by SDS-PAGE of cell extracts (FIG. 6A, lane 2 at 42° C.).

Figure 6A:
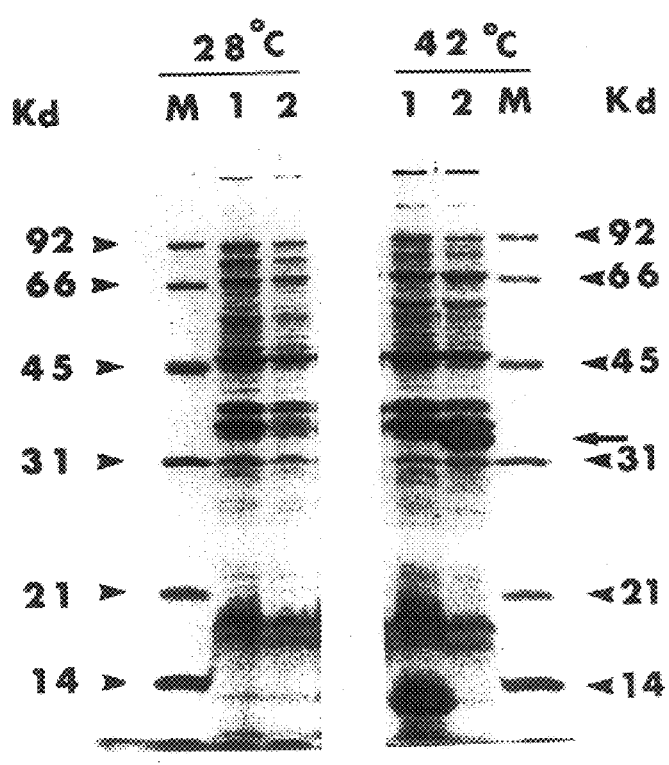
FIGS. 6A and 6B are autoradiographs of sodium dodecyl sulfate polyacrylamide (SDS-PAGE) gels demonstrating the expression of the polypeptide of the present invention as a fusion protein in bacteria.

In FIG. 6A, lanes 1 represent the SDS-PAGE results for bacterial extracts transformed with a vector without the cDNA; lanes 2 represent the results of extracts transformed by a cDNA-bearing vector. The arrow next to the 31 kD markers in FIG. 6A represents the position of the polypeptide of the present invention.

Figure 6B:
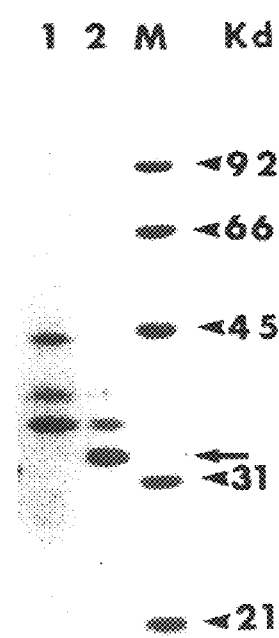

Since this protein, like many other bacterial fusion proteins was insoluble, the insoluble fraction of the protein extract was partially purified by extraction with 7M urea. This resulted in a protein preparation containing the fusion protein and about seven to eight other bacterial proteins (see the SDS-PAGE of cell extracts in FIG. 6B, lane 2). The fusion protein was estimated to represent about 20% of the total protein mass. After dialysis, the entire 7M urea protein extract (containing the growth factor fusion protein) was applied to normal NIH3T3 cells at various concentrations and the cells incubated in DMEM plus 0.5% serum for five days. Two controls were used involving cells which either received nothing, (except DMEM +0.5% calf serum) or cells which received the insoluble, 7M urea-extracted protein fraction from bacteria expressing only the pEx34C vector (without a cDNA insert). The results are shown graphically in FIG. 7A.

Figure 7A:
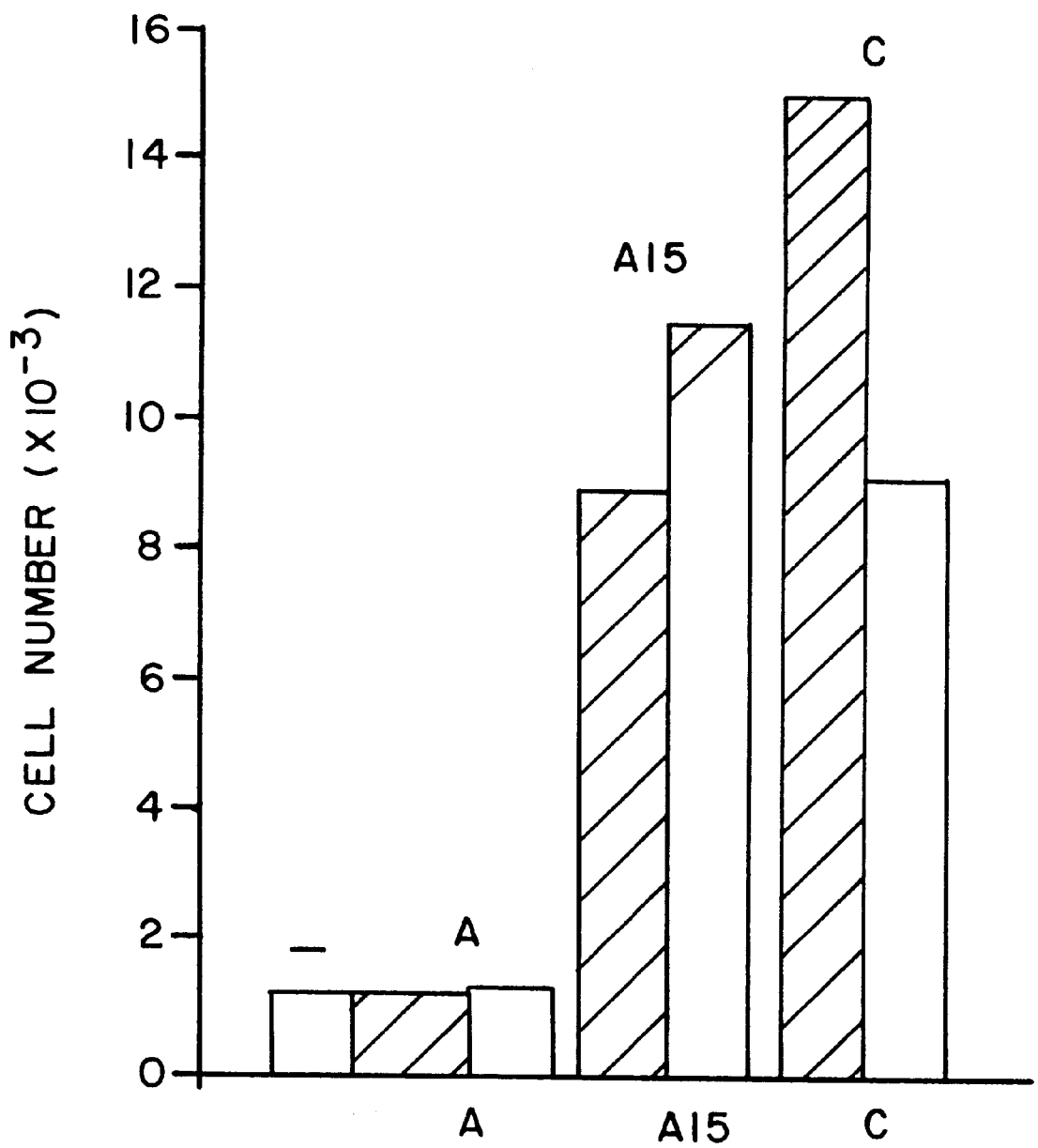
FIGS. 7A and 7B are graphs demonstrating the growth-promoting effects of the polypeptide of the present invention on the growth of NIH3T3 cells.

In FIG. 7A; the symbol "-" represents no addition of extract, "A" represents addition of cell extracts from cells which received the vector without an insert, "A15" represents addition of conditioned medium from the A15T-transformed cell line mentioned above; and "C" represents addition of cell extracts from cells transformed with vectors encoding the fusion protein of the present invention. In FIG. 7A, the striped bars represent: for A15 a 1 to 2 dilution of the conditioned medium; for C an amount of bacterial extract estimated to correspond to 100 nanograms/ml of the fusion protein, and for A an equivalent amount of bacterial proteins extracted from bacteria expressing the vector alone. The solid bars in FIG. 7A represent: for A15 a 1 to 4 dilution of the conditioned medium, for C an amount of extract corresponding to 40 nanograms/ml of the fusion protein, and for A an equivalent amount of extract from bacteria expressing the vector alone.

While cells in the control cultures did not proliferate appreciably in 5 days, cells receiving the fusion protein (containing the growth factor) showed appreciable growth (FIG. 7), in a dose-dependent fashion. These data therefore show that a growth factor gene was isolated and that the protein it encodes was expressed in bacteria.

EXAMPLE 8: EXPRESSION OF THE MAMMALIAN GROWTH FACTOR IN MAMMALIAN CELLS

The plasmid p9BKS3A, containing the cDNA encoding the mammalian growth factor of the present invention, was transfected into monkey COS cells. COS-1 cells (Gluzman, Y. *Cell.* 23: 175, 1981 incorporated by reference) are a line of simian cells which constitutively express the SV40 large T antigen, and thus, any DNA molecule containing the SV40 replication origin (such as plasmid P9BKS3A) introduced into these cells can be amplified and expressed. COS cells are available as ATCC CRL 1650 and ATCC CRL 1651 from the American Type culture collection Rockville, Md.). By using such a system, the cDNA encoding the growth factor of the present invention was amplified and its gene product was overproduced.

COS cells were plated at $1 \times 10^6$ cells per petri dish and incubated overnight before transfection. Three micrograms of recombinant plasmid DNA (p9BKS3A, FIG. 4C) were transfected using the DEAE-dextran technique followed by chloroquine treatment (Luthman, H. et al *Nuc. Acid Res.* 11: 1265–1308, 1983) to improve the uptake of the transfected DNA. After 45 hours, the transfected cells were labeled with $^{35}$S-methionine for two hours (200 microci per ml) and total cell lysates were prepared as follows. Cells were washed in ice cold STE buffer (15mM NaCl; 10 mM Tris pH 7.2; 1 mM EDTA) lysed in RIPA buffer (10 mM Tris pH 7.4; 0.15M NaCl; 1% sodium deoxycholate; 1% Nonidet P-40; 1 mM EDTA; 10 mM KCl; 1% APROTININ), the cell lysate was vortexed for 30 seconds and then centrifuged at 4° C. in a microfuge for 30 seconds. The supernatant was recovered and the same number of counts for each sample were analyzed by sodium dodecylsulfate polyacrylamide gel electrophoresis (SDS-PAGE). The results are shown in FIG. 8.

Figure 8:
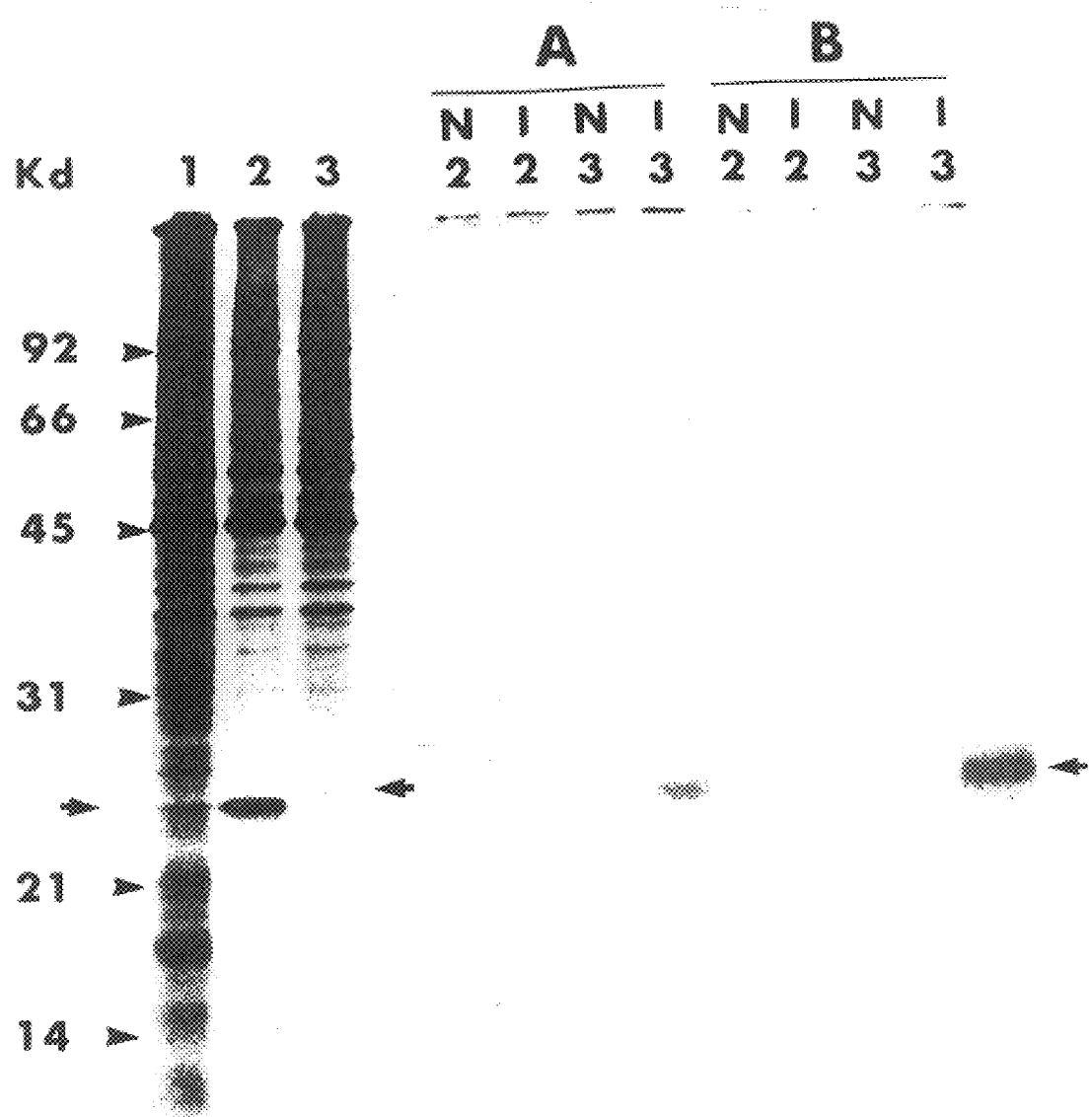
FIG. 8 is an autoradiograph of an SDS-PAGE gel demonstrating the production of the polypeptide of the present invention by transfected COS cells, and its specific immunoprecipitation by rabbit antibodies directed against said polypeptide.

In FIG. 8, the first three lanes from the left contain (1) labeled total cell extract proteins from COS cells not transfected with any DNA; (2) COS cells transfected with the vector without any inserted DNA; (3) contains labeled total proteins from cells transfected with the vector with the inserted cDNA encoding the growth factor of the present invention. The arrow between molecular weight markers 21 and 31 kD on the right side indicates the polypeptide of the present invention (very faint).

As can be seen from FIG. 8, lane 3 a band of about 24 kD not present in the control cells, was visualized. The smearing of the band is probably due to post-translational modifications such as glycosylation. When cos cell extracts were reacted with a rabbit antiserum directed against the growth factor of the present invention (raised by immunization against the bacterial fusion protein), a 24 kD protein was specifically precipitated by two different antisera A and B (right hand side of FIG. 8, labelled A and B; "N" represents preimmune and "I" represents immune serum).

Figure 7B:
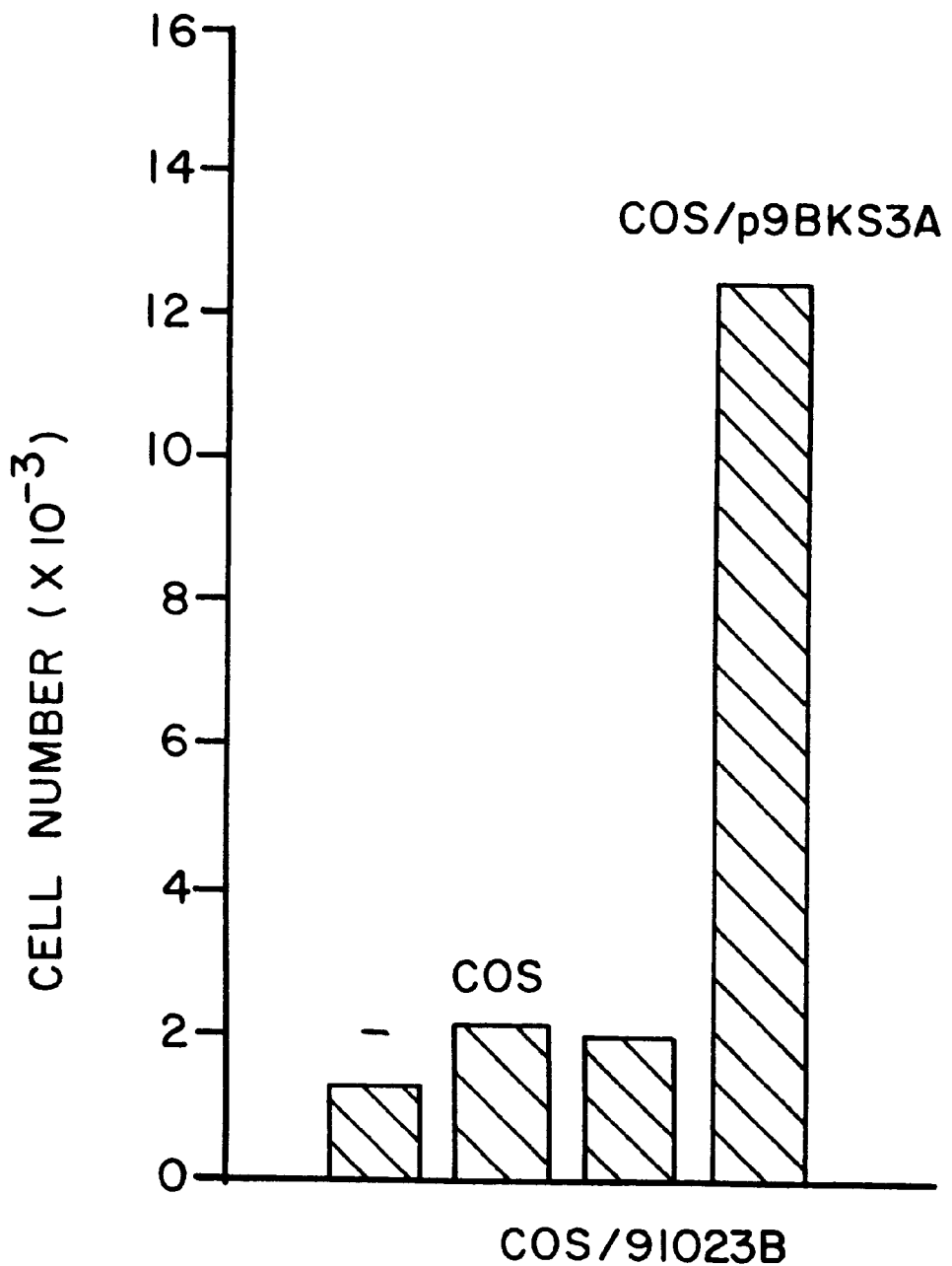

Extracts of COS cells (transfected with plasmid p9BKS3A) were also applied to mouse NIH3T3 cells incubated in DMEM plus 0.5% calf serum in order to probe for growth factor activity. In FIG. 7B the cells received: no addition (–), extracts from non-transfected COS cells (COS), extracts from cells transfected with the vector alone (COS/91023B) or extracts from cells transfected with the vector encoding the growth factor of the present invention (COS/p9BKS3A). As shown in FIG. 7B, soluble protein extracts of sonically-disrupted, transfected COS cells produced a considerable increase in cell number during the four days of incubation whereas control extracts (from COS cells which were not transfected at all) did not.

Example 9: SECRETION OF THE MAMMALIAN GROWTH FACTOR FROM TRANSFECTED CELLS

To study the processing of the mammalian growth factor of the present invention, the COS-1 cells transfected with plasmid p9BKS3A of Example 8 were labeled with $^{35}$S-methionine (1,200 Ci per mmol, New England Nuclear, Boston, Mass.) at 200 microci per ml 48–52 hours after transfection in the presence or absence of tunicamycin (Tu, 10 micrograms per ml, Calbiochem-Behring, San Diego, Calif.), cell extracts prepared as in Example 8 above), and the cell extracts or the culture media were subjected to immunoprecipitation using the rabbit antiserum specific for the mammalian growth factor of the present invention described above. The immunoprecipitates were then run on 12.5% SDS-PAGE. The results are shown in FIGS. 9A–C.

Figure 9A:
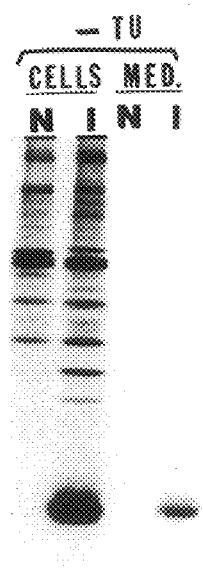
FIGS. 9A–C are autoradiographs of SDS-PAGE gels showing the secretion of the polypeptide of the present invention in the absence (A) or presence (B) of tunicamycin and of the in vitro translation product (C) which was immunoprecipitated by rabbit antibodies directed against the polypeptide of the present invention. Presented in FIG. 9D is the amino acid sequence of the polypeptide showing the sites of glycosylation, cleavage of the signal sequence and potential sites of intramolecular disulfide bonds.
Figure 9B:
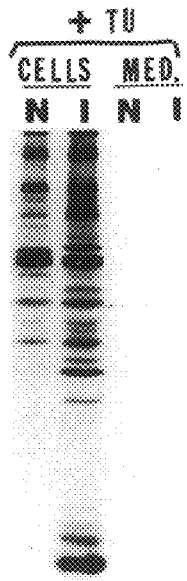
Figure 9C:
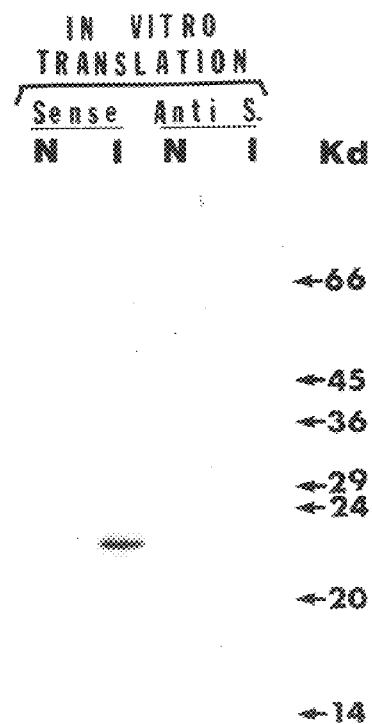

In FIGS. 9A–C, N=non-immune (or control) sera; I=immune sera. Present on the right are molecular weight markers (in kilodaltons, Kd). Present in FIG. 9D is the amino acid sequence of the polypeptide of the present invention. Arrows indicate the positions of cleavage of the pre-protein, stars under the sequence indicate potential glycosylation signals and dots indicate potential cysteine residues which could form intramolecular disulfide bonds; the underlined amino acid residues are the presumptive signal sequence.

As can be seen in FIG. 9A an appreciable proportion of the mammalian growth factor of the present invention, migrating with an apparent molecular weight of 22,000 to 23,000 Daltons, is found in the culture medium as would be expected for a secreted protein (lane 2) and was specifically immunoprecipitated with immune serum.

In addition, the mature growth factor of the present invention as produced by mammalian cells is a glycoprotein as demonstrated by the fact that incubation of cells with tunicamycin, a specific inhibitor of N-linked glycosylation, resulted in the production of a protein with a reduced apparent molecular weight (approximately 19,000 Daltons) which was not efficiently secreted (Lane 2, FIG. 9B). The molecular weight of the protein produced in vivo in the presence of tunicamycin was compared with that of the protein translated in vitro in order to determine whether any additional processing of the mammalian growth factor of the present invention occurred, such as cleavage of the signal peptide. The mammalian growth factor RNA and an "antisense" RNA were transcribed in vitro using SP6 polymerase (Promega Biotech, Madison, Wis.), the resulting RNAs translated in vitro using a rabbit reticulocyte translation system (Promega Biotech), and the product immunoprecipitated with rabbit antiserum generated against the mammalian growth factor.

FIG. 9C shows that the primary in vitro translation product of the mammalian growth factor obtained from the reticulocyte translation system had a molecular weight of approximately 22,000 Daltons, in agreement with that predicted from the amino acid sequence (FIG. 9C, lane 2). This is about 3,000 Daltons higher than the unglycosylated protein produced in vivo, indicated that the primary translation product is processed to a mature form lacking approximately 30 amino acid residues. Neither non-immune serum nor the translation product of antisense RNA resulted in the immunoprecipitation of any product.

To determine whether the site of cleavage corresponds to the putative signal peptide, the N-terminus of the secreted mammalian growth factor protein was determined as described below.

COS-1 cells transfected with plasmid p9BKS3A were grown for 48 h after transfection. The cells were washed twice in phosphate-buffered saline and a small volume of media (Earle's MEM, Select Amine Kit, Difco, available from Sigma Chemical Co., St. Louis, Mo.) containing either [$^3$H]leucine or [$^3$H]arginine, replacing the corresponding cold amino acid, was added and the cells grown for a further 7 h. The media was removed, clarified by centrifugation and the mammalian growth factor was immunoprecipitated as described in Delli-Bovi et al., *Cell* 50: 729–737, 1987, incorporated by reference. The labeled protein was released from protein A-Sepharose 4B beads (Pharmacia Fine Chemicals, Piscataway, New Jersey) by heating at 80° C. for 10 minutes in 10 mM Tris (pH 7.6), 1 mM EDTA, 0.1% SDS. A small aliquot of this material was run on SDS-PAGE and fluorographed to verify its purity. The protein/antibody complex was precipitated with trichloroacetic acid to remove SDS, the precipitate resuspended in 50% trifluoroacetic acid, loaded directly onto a protein sequencer (Applied Biosystems model 470A) and sequenced as described in Hewick et al., *J. Biol. Chem.*, 256:7990, 1981, incorporated by reference. Fractions containing labeled residues were aligned with the predicted amino acid sequence to determine the amino terminal residue.

The results obtained indicated that the mature mammalian growth factor protein had two possible N terminal amino acids, either Ala31 or Pro32 (arrows under sequence in FIG. 9D), and had lost the signal peptide. Therefore, as is the case for normal mammalian secretory proteins, the pre-protein co-translationally entered the endoplasmic reticulum (ER) through the normal secretory pathway where the signal peptide was cleaved at residue 30 or 31, and was glycosylated in the ER and the Golgi apparatus before being finally secreted into the culture medium as a mature protein of either 175 or 176 amino acids. Immunofluorescence staining of transfected COS-1 cells expressing the mammalian growth factor of the present invention provided a visual demonstration of the localization of this growth factor in the ER and cytoplasm when the cells were made permeable to the antibodies (data not shown). When the cells were fixed with formalin, most of the cross-reacting material was visualized on the cell surface (data not shown).

Example 10: SECRETION AND STABILIZATION OF THE MAMMALIAN GROWTH FACTOR BY HEPARIN The time course of the secretion of the mammalian growth factor from COS-1 cells transfected with the p9BKS3A expression plasmid was examined. Since the biological activity of fibroblast growth factors are known to be potentiated and/or stabilized by heparin, the effect of the presence of heparin on the stability of the secreted mammalian growth factor of the present invention was examined. Cells were pulse-labeled for twenty minutes with $^{35}$S-methionine, washed, and the label chased with an excess of cold methionine in the presence or absence of heparin (45 micrograms per ml, Sigma Chemical Co., St. Louis, Mo.). The presence of the mammalian growth factor protein contained in the cell extract (C) or the medium (M) of the transfected cultures was determined by SDS-PAGE after immunoprecipitation. Presented on the left in FIGS. 10A–D are molecular weight markers (in kilodaltons, Kd); the large arrow indicates the position of migration of the polypeptide of the present invention (approximately 23 Kd). In addition, N=non-immune (control) sera and I=immune sera. It should be noted that in all of the data presented in FIGS. 10A–D, only immune sera was capable of immunoprecipitating any product.

Figures 10A, 10B:
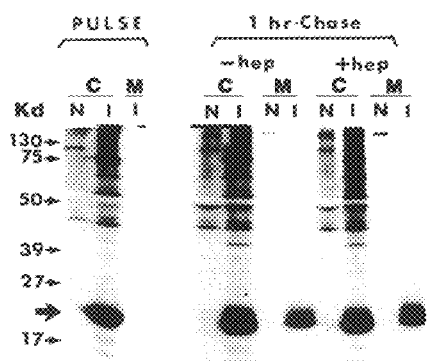
FIGS. 10A–D are autoradiographs an SDS-PAGE gels showing the kinetics of secretion of the polypeptide of the present invention, after a 1 hour pulse (A), a 1 hour chase (B), a 7 hour chase (C) or a 19 hour chase (D) and its stabilization by heparin.
Figure 10C:
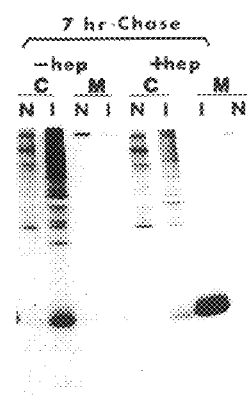
Figure 10D:
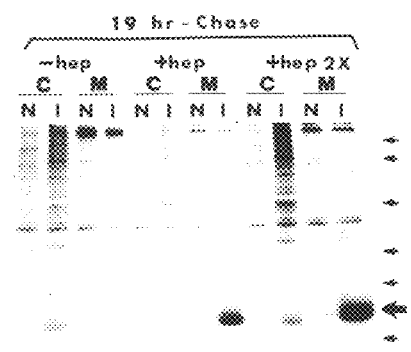

FIG. 10B shows that one hour after the pulse, there was an approximate 60:40 partition of the mammalian growth factor between the intracellular and the extracellular fraction, respectively, both in the presence (lanes 4–8) or absence (lanes 1–4) of heparin. After a seven hour chase (FIG. 10C), there was a dramatic difference between the two types of cultures. In the absence of heparin (lanes 1–4), the mammalian growth factor of the present invention had practically disappeared from the culture medium (lane 4) and only a small amount of the protein remained in the cells (lane 2). In the presence of heparin (lanes 5–8), a large quantity of the mammalian growth factor could be detected in the medium. This difference was even more pronounced after a nineteen hour chase (FIG. 10D). No labelled protein was detectable in control cultures (lanes 1–4), while those incubated with heparin (lanes 5–8) still contain a significant amount of the factor in the culture medium (lane 8). Increasing the concentration of heparin (to 90 micrograms per ml, lanes 9–12) resulted in an even higher stability of the protein (lane 12), although this effect was not always reproducible. Thus, the presence of heparin increased the half-life of the mammalian growth factor protein after secretion suggesting that it may protect the protein from protease attack and/or help in the formation of a temperature-stable complex.

Figure 11:
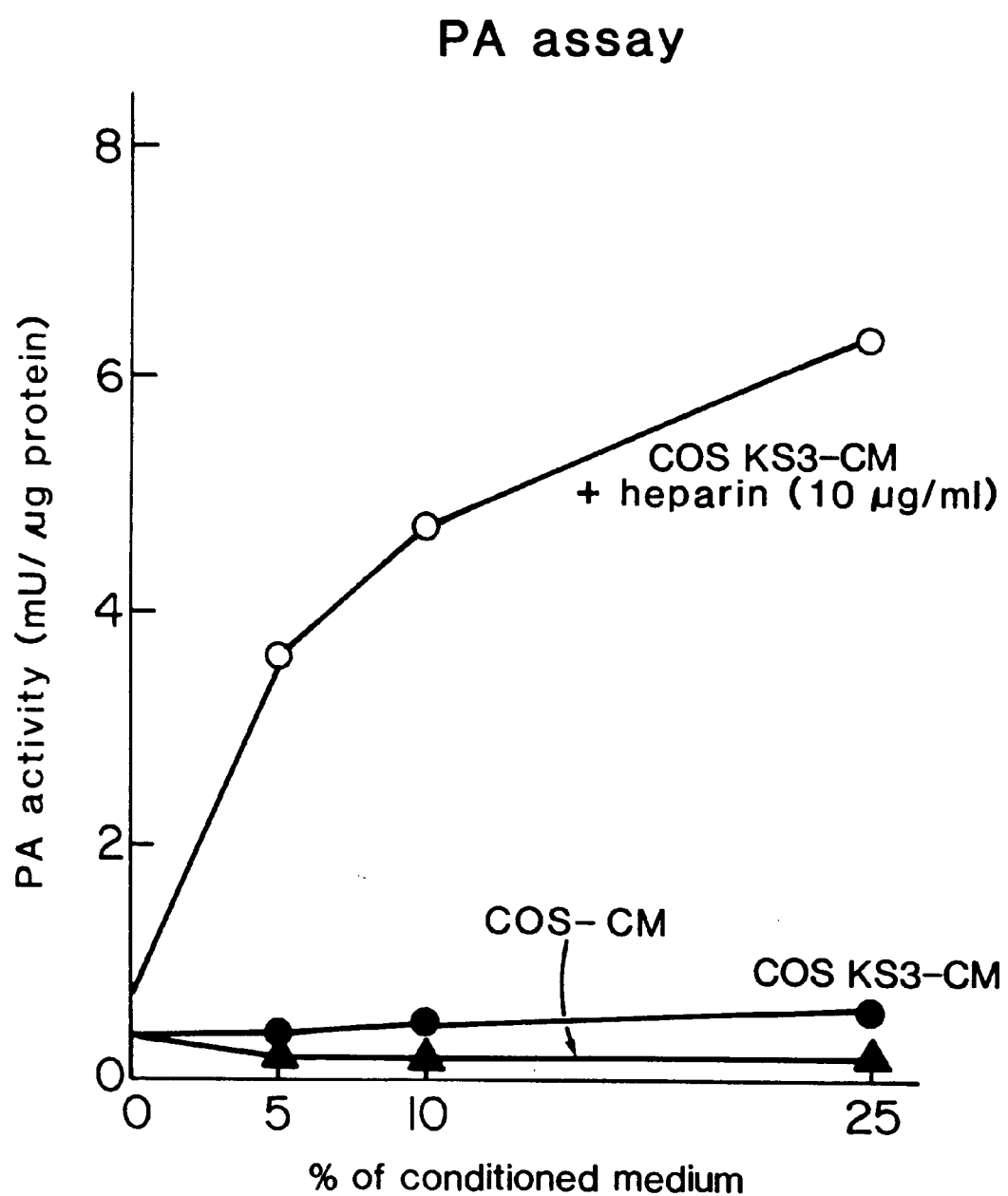
FIG. 11 is a graph showing the induction of plasminogen activator by bovine capillary endothelial (BCE) cells treated with the polypeptide of the present invention.

The effect of the mammalian growth factor of the present invention on the growth of bovine capillary endothelial (BCE) cells was examined. The induction or plasminogen activator (PA) activity, DNA synthesis and cell proliferation in the presence of the mammalian growth factor of the present invention was compared with that obtained with basic fibroblast growth (bFGF, Amgen Biologicals, Thousand Oaks, Calif.) as these are activities known to be affected by bFGF. Plasminogen activator activity was assayed as described in Gross et al. *J. Cell Biol.* 95:924–981, 1982 (incorporated by reference). Conditioned medium produced by COS-1 cells transfected with the p9BKS3A plasmid was used as the source of the mammalian growth factor of the present invention. This medium effectively stimulated PA production in BCE cells if the medium was assayed in the presence of heparin (FIG. 11). In the absence of heparin, there was practically no stimulatory activity above that obtained by control COS-1 cell condition medium (FIG. 11). Heparin by itself had no stimulatory effect. Neutralizing antibodies to bFGF (as described in Presta, M. et al., *Mol. Cell. Biol.* 6:4060–4066, 1986) were unable to block the stimulation of PA production induced by the mammalian growth factor of the present invention. This result indicated that the stimulatory effect was not due to bFGF which might have been released from the COS-1 cells.

The culture medium from transfected COS-1 cells was also capable of stimulating DNA synthesis in growth arrested BCE cells. Confluent monolayers of BCE cells were maintained for seven days in DMEM plus 5% calf serum. The medium was then replaced with fresh DMEM plus 0.5% calf serum containing various additions detailed below. After 20 hours, the cells were labeled with 1 microCi per ml of methyl-[$^3$H]thymidine (6.7 Ci per mmol; New England Nuclear, Boston, Mass.) for 3 hours. Cells were washed twice with phosphate buffered saline and the incorporation of label into trichloroacetic acid preciptable material was determined.

Figure 12:
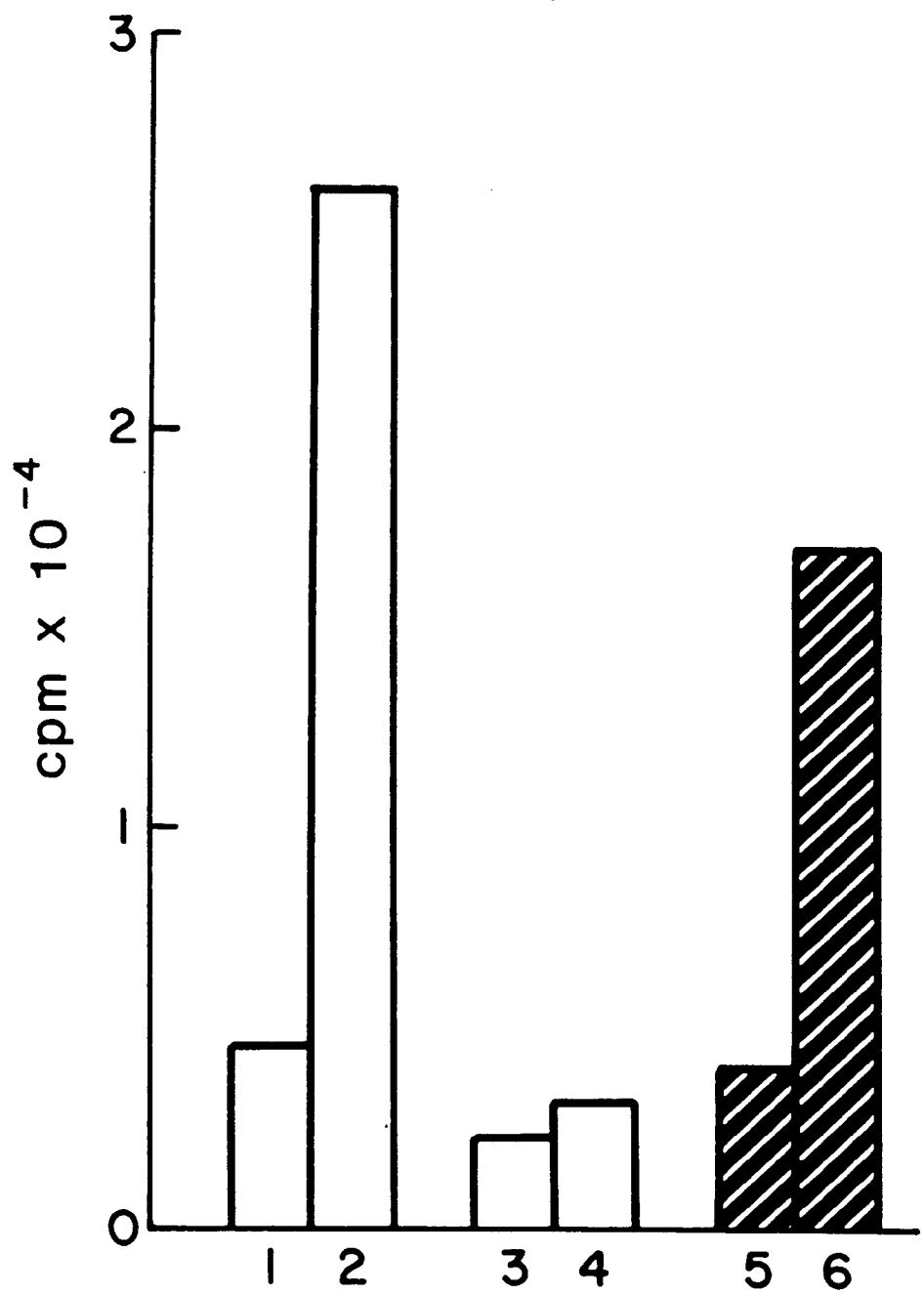
FIG. 12 is a bar graph showing the induction of DNA synthesis in BCE cells treated with either basic fibroblast growth factor or the polypeptide of the present invention.

The results of the above-described experiment are shown in FIG. 12 where lane 1 is control BCE cells, lane 2, BCE cells plus bFGF (10 ng per ml); lane 3, BCE cells incubated with conditioned medium (CM) from control COS-1 cells at a 1:20 dilution; lane 4, CM plus heparan (10 micrograms per ml); lane 5, BCE cells incubated with conditioned medium from COS-1 cells expressing the growth factor of the present invention (COS-K-FGF-CM) at a 1:20 dilution; lane 6, BCE cells incubated with COS-K-FGF-CM plus heparin (10 micrograms per ml).

Conditioned medium, obtained from COS-1 cells expressing the growth factor of the present invention plus heparin (FIG. 12, lane 5) was almost as stimulatory as medium supplemented with bFGF (obtained from Amgen Biologicals, Thousand Oaks, Calif.), (FIG. 12, lane 2) while medium from control cells was non-stimulatory (FIG. 12, lane 3). The proliferative effect of the mammalian growth factor of the present invention was also apparent when the number of cells was determined.

The results presented above show that the mammalian growth factor of the present invention acted as a growth factor for capillary endothelial cells in culture.

In addition FIG. 13 shows that the mammalian growth factor could also promote growth of the human endothelial cells lining large vessels. In this experiment, cultures of human umbilical cord vein endothelial cells (HUVE) were plated on multiwell dishes (each well having a surface of about 1.5 cm$^2$) in a culture medium consisting of DMEM/F12 Medium mixed 1:1 (GIBCO, Grand Island, N.Y.) supplemented with 20% fetal calf serum and either endothelial cells growth supplement at 120 micrograms/ml (ECGS, Collaborative Research, Bedford, Mass.) or the growth factor of the present invention (K-FGF, i.e. conditioned medium from COS cell transfected with the p9BKS3A plasmid diluted to a final concentration of 5%) with or without heparin (90 micrograms/ml). The media were changed every two days and the final cell number determined at day 7.

It can be seen from the data presented in FIG. 13 that the HUVE cells did not proliferate in absence of added growth factors (−) or with heparin alone (Hep.). The growth factor of the present invention (K-FGF+HEP) was approximately as effective as ECGS+heparin in promoting proliferation of HUVE cells. Although the growth promoting effect of the polypeptide of the present invention was decreased in the absence of heparin, it was still very substantial (K-FGF, FIG. 13).

What is claimed is:

1. A homogeneous K-FGF polypeptide having a molecular weight of about 19,000 daltons when produced by culturing COS-1 cells containing the plasmid p9BKS3A under the conditions suitable for expression of the protein and in the presence of tunicamycin.

* * * * *